(12) United States Patent
Crawford et al.

(10) Patent No.: US 11,969,224 B2
(45) Date of Patent: Apr. 30, 2024

(54) DRILL GUIDE FIXTURES, CRANIAL INSERTION FIXTURES, AND RELATED METHODS AND ROBOTIC SYSTEMS

(71) Applicant: GLOBUS MEDICAL, INC., Audubon, PA (US)

(72) Inventors: Neil Crawford, Chandler, AZ (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 238 days.

(21) Appl. No.: 17/524,240

(22) Filed: Nov. 11, 2021

(65) Prior Publication Data

US 2022/0133418 A1    May 5, 2022

Related U.S. Application Data

(63) Continuation of application No. 16/535,223, filed on Aug. 8, 2019, now Pat. No. 11,744,655, which is a
(Continued)

(51) Int. Cl.
*A61B 34/30*     (2016.01)
*A61B 17/16*     (2006.01)
(Continued)

(52) U.S. Cl.
CPC .............. *A61B 34/30* (2016.02); *A61B 34/10* (2016.02); *A61B 34/20* (2016.02); *A61B 90/14* (2016.02);
(Continued)

(58) Field of Classification Search
CPC ......... A61B 34/30; A61B 34/10; A61B 34/20; A61B 90/14; A61B 2034/107; A61B 2034/2057; A61B 17/1615; A61B 17/1703
See application file for complete search history.

(56) References Cited

U.S. PATENT DOCUMENTS

| 2,496,089 A | 1/1950 | Goldfield et al. |
| 4,150,293 A | 4/1979 | Franke |
(Continued)

FOREIGN PATENT DOCUMENTS

| CN | 201139550 Y | 10/2008 |
| CN | 101697869 A | 4/2010 |
(Continued)

OTHER PUBLICATIONS

US 8,231,638 B2, 07/2012, Swarup et al. (withdrawn)

*Primary Examiner* — Kelly J Bekker
*Assistant Examiner* — Mohammed S Adam

(57) ABSTRACT

A drill guide fixture may be configured to prepare a skull for attachment of a cranial insertion fixture. The drill guide fixture may include a central drill guide and a bone anchor guide at a base of the drill guide fixture. The central drill guide may define a central drill guide hole therethrough, wherein the central drill guide hole has a first opening at a base of the drill guide fixture and a second opening spaced apart from the base of the drill guide fixture. The bone anchor drill guide may define a bone anchor drill guide hole therethrough, and the bone anchor drill guide hole may be offset from the central drill guide hole in a direction that is perpendicular with respect to a direction of the central drill guide hole. Related cranial insertion fixtures, robotic systems, and methods are also discussed.

16 Claims, 41 Drawing Sheets

Related U.S. Application Data continuation-in-part of application No. 16/209,266, filed on Dec. 4, 2018, now Pat. No. 11,602,402.

(51) Int. Cl.
- *A61B 17/17* (2006.01)
- *A61B 34/10* (2016.01)
- *A61B 34/20* (2016.01)
- *A61B 90/14* (2016.01)

(52) U.S. Cl.
CPC ....... *A61B 17/1615* (2013.01); *A61B 17/1703* (2013.01); *A61B 2034/107* (2016.02); *A61B 2034/2057* (2016.02)

(56) References Cited

U.S. PATENT DOCUMENTS

| | | |
|---|---|---|
| 4,592,352 A | 6/1986 | Patil |
| 4,638,798 A | 1/1987 | Shelden et al. |
| 4,706,665 A | 11/1987 | Gouda |
| 4,833,972 A | 5/1989 | Bohusch et al. |
| 5,078,140 A | 1/1992 | Kwoh |
| 5,116,344 A | 5/1992 | Sundqvist |
| 5,176,689 A | 1/1993 | Hardy et al. |
| 5,246,010 A | 9/1993 | Gazzara et al. |
| 5,354,314 A | 10/1994 | Hardy et al. |
| 5,397,323 A | 3/1995 | Taylor et al. |
| 5,423,832 A | 6/1995 | Gildenberg |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,073,512 A | 6/2000 | Mccormick et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,298,262 B1 | 10/2001 | Franck et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,463,319 B1 | 10/2002 | Bucholz |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,491,699 B1 | 12/2002 | Henderson et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,529,765 B1 | 3/2003 | Franck |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,609,022 B2 | 8/2003 | Vilsmeier et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,676,669 B2 | 1/2004 | Charles et al. |
| 6,694,162 B2 | 2/2004 | Hartlep |
| 6,701,173 B2 | 3/2004 | Nowinski et al. |
| 6,741,883 B2 * | 5/2004 | Gildenberg ............ A61B 90/36 600/417 |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,840,895 B2 | 1/2005 | Perry et al. |
| 6,856,826 B2 | 2/2005 | Seeley et al. |
| 6,856,827 B2 | 2/2005 | Seeley et al. |
| 6,859,660 B2 | 2/2005 | Vilsmeier |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,008,362 B2 | 3/2006 | Fitzgibbon |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,206,626 B2 | 4/2007 | Quaid, III |
| 7,206,627 B2 | 4/2007 | Abovitz et al. |
| 7,217,276 B2 | 5/2007 | Henderson et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |

(56) References Cited

U.S. PATENT DOCUMENTS

| | | |
|---|---|---|
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,616,735 B2 | 11/2009 | Maciunas et al. |
| 7,623,902 B2 | 11/2009 | Pacheco |
| 7,625,383 B2 | 12/2009 | Charles et al. |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,747,311 B2 | 6/2010 | Quaid, III |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,776,056 B2 | 8/2010 | Henderson et al. |
| 7,787,699 B2 | 8/2010 | Mahesh et al. |
| 7,794,469 B2 | 9/2010 | Kao et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,292 B2 | 11/2010 | Quaid et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| 7,892,243 B2 | 2/2011 | Stuart |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,328 B2 | 4/2011 | Urquhart et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,963,913 B2 | 6/2011 | Devengenzo et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,981,122 B2 | 7/2011 | Labadie et al. |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,010,180 B2 | 8/2011 | Quaid et al. |
| 8,019,045 B2 | 9/2011 | Kato |
| 8,021,310 B2 | 9/2011 | Sanborn et al. |
| 8,035,685 B2 | 10/2011 | Jensen |
| 8,041,459 B2 | 10/2011 | Sutherland et al. |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,095,200 B2 | 1/2012 | Quaid, III |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,175,677 B2 | 5/2012 | Sayler et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |

(56) References Cited

U.S. PATENT DOCUMENTS

| | | |
|---|---|---|
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,597 B2 | 4/2013 | Kao et al. |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,480,566 B2 | 7/2013 | Farr |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,132 B2 | 8/2013 | Norton |
| 8,500,722 B2 | 8/2013 | Cooper |
| 8,500,728 B2 | 8/2013 | Newton et al. |
| 8,503,759 B2 | 8/2013 | Greer et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,509,503 B2 | 8/2013 | Nahum et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,529,582 B2 | 9/2013 | Devengenzo et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Greer et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,601,667 B2 | 12/2013 | Norton |
| 8,602,971 B2 | 12/2013 | Farr |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,747,418 B2 | 6/2014 | Qureshi et al. |
| 8,749,189 B2 | 6/2014 | Nowlin et al. |
| 8,749,190 B2 | 6/2014 | Nowlin et al. |
| 8,758,263 B1 | 6/2014 | Rahimian et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |

(56) References Cited

U.S. PATENT DOCUMENTS

| | | |
|---|---|---|
| 8,844,789 B2 | 9/2014 | Shelton, IV et al. |
| 8,845,655 B2 | 9/2014 | Henderson et al. |
| 8,855,822 B2 | 10/2014 | Bartol et al. |
| 8,857,821 B2 | 10/2014 | Norton et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Tott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,911,499 B2 | 12/2014 | Quaid et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,132,053 B1 | 9/2015 | Ferreri et al. |
| 9,192,446 B2 | 11/2015 | Piferi et al. |
| 9,215,968 B2 | 12/2015 | Schostek et al. |
| 9,237,861 B2 | 1/2016 | Nahum et al. |
| 9,237,931 B2 | 1/2016 | Gowda et al. |
| 9,308,050 B2 | 4/2016 | Kostrzewski et al. |
| 9,326,823 B2 | 5/2016 | McMillan et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,492,241 B2 | 11/2016 | Joskowicz et al. |
| 9,498,290 B2 | 11/2016 | Plferi et al. |
| 9,521,966 B2 | 12/2016 | Schwartz |
| 9,554,864 B2 | 1/2017 | Taylor et al. |
| 9,587,878 B2 | 3/2017 | Paydar et al. |
| 9,592,096 B2 | 3/2017 | Maillet et al. |
| 9,592,172 B2 | 3/2017 | Ferreri et al. |
| 9,600,138 B2 | 3/2017 | Thomas et al. |
| 9,636,185 B2 | 5/2017 | Quaid et al. |
| 9,649,168 B2 | 5/2017 | Rahimian et al. |
| 9,734,632 B2 | 8/2017 | Thomas et al. |
| 9,750,432 B2 | 9/2017 | Nahum et al. |
| 9,750,465 B2 | 9/2017 | Engel et al. |
| 9,757,203 B2 | 9/2017 | Hourtash et al. |
| 9,755,682 B2 | 10/2017 | Quaid et al. |
| 9,788,906 B2 | 10/2017 | Piron et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,827,053 B2 | 11/2017 | Chen et al. |
| 9,833,265 B2 | 11/2017 | Donner et al. |
| 9,833,254 B1 | 12/2017 | Barral et al. |
| 9,844,414 B2 | 12/2017 | Fischer et al. |
| 9,848,922 B2 | 12/2017 | Tohmeh et al. |
| 9,901,400 B2 | 2/2018 | Gowda et al. |
| 9,925,011 B2 | 3/2018 | Gombert et al. |
| 9,925,013 B2 | 3/2018 | Dell et al. |
| 9,931,025 B1 | 4/2018 | Graetzel et al. |
| 10,028,874 B2 | 7/2018 | Koch |
| 10,034,717 B2 | 7/2018 | Miller et al. |
| 10,039,476 B2 | 8/2018 | Nahum et al. |
| 10,039,507 B2 | 8/2018 | Patil et al. |
| 10,070,940 B2 | 9/2018 | Bailey et al. |
| 10,076,844 B2 | 9/2018 | Rizk |
| 10,123,841 B2 | 11/2018 | Kim et al. |
| 10,231,792 B2 | 3/2019 | Shiels et al. |
| 10,376,331 B2 | 8/2019 | Cooper et al. |
| 10,434,322 B2 | 10/2019 | Lee et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0027463 A1* | 1/2008 | Labadie ............ A61B 17/1778 606/130 |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0042111 A1 | 2/2010 | Qureshi |
| 2010/0042112 A1 | 2/2010 | Qureshi et al. |
| 2010/0125286 A1 | 5/2010 | Wang et al. |
| 2010/0130986 A1 | 5/2010 | Mailloux et al. |
| 2010/0168759 A1 | 7/2010 | Yoon et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |

(56) References Cited

U.S. PATENT DOCUMENTS

| | | |
|---|---|---|
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0190965 A1 | 7/2012 | Schaerer et al. |
| 2012/0190966 A1 | 7/2012 | Schaerer et al. |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0053867 A1 | 2/2013 | Gowda et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0024927 A1 | 1/2014 | Piferi et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0296871 A1 | 10/2014 | Chen et al. |
| 2014/0299648 A1 | 10/2014 | Shelton, IV et al. |
| 2014/0303434 A1 | 10/2014 | Farritor et al. |
| 2014/0303486 A1 | 10/2014 | Baumgartner et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0011866 A1 | 1/2015 | Baumgartner |
| 2015/0039034 A1 | 2/2015 | Frankel et al. |
| 2015/0073433 A1 | 3/2015 | Schaerer et al. |
| 2015/0085970 A1 | 3/2015 | Bouhnik et al. |
| 2015/0109427 A1 | 4/2015 | Wood et al. |
| 2015/0146847 A1 | 5/2015 | Liu |
| 2015/0150524 A1 | 6/2015 | Yorkston et al. |
| 2015/0196261 A1 | 7/2015 | Funk |

(56) References Cited

U.S. PATENT DOCUMENTS

| | | |
|---|---|---|
| 2015/0213633 A1 | 7/2015 | Chang et al. |
| 2015/0265365 A1* | 9/2015 | Andrews ............ A61B 18/1477 606/130 |
| 2015/0335390 A1 | 11/2015 | Gill |
| 2015/0335480 A1 | 11/2015 | Alvarez et al. |
| 2015/0342647 A1 | 12/2015 | Frankel et al. |
| 2015/0351860 A1 | 12/2015 | Piron et al. |
| 2015/0374217 A1 | 12/2015 | Sinofsky |
| 2016/0005194 A1 | 1/2016 | Schretter et al. |
| 2016/0038253 A1 | 2/2016 | Piron et al. |
| 2016/0166329 A1 | 6/2016 | Langan et al. |
| 2016/0193009 A1 | 7/2016 | Gowda et al. |
| 2016/0235480 A1 | 8/2016 | Scholl et al. |
| 2016/0249990 A1 | 9/2016 | Glozman et al. |
| 2016/0278870 A1 | 9/2016 | Quaid et al. |
| 2016/0296242 A1 | 10/2016 | Pak et al. |
| 2016/0296293 A1 | 10/2016 | Gill et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2016/0361132 A1 | 12/2016 | Piferi et al. |
| 2017/0055819 A1 | 3/2017 | Hansen et al. |
| 2017/0065355 A1 | 3/2017 | Ross et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0165005 A1 | 6/2017 | Kheradpir et al. |
| 2017/0202629 A1 | 7/2017 | Maillet et al. |
| 2017/0202631 A1 | 7/2017 | Piferi et al. |
| 2017/0209324 A1 | 7/2017 | Smith |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0258535 A1 | 9/2017 | Crawford |
| 2017/0265943 A1 | 9/2017 | Sela et al. |
| 2017/0265947 A1 | 9/2017 | Dyer et al. |
| 2017/0273748 A1 | 9/2017 | Hourtash et al. |
| 2017/0296277 A1 | 10/2017 | Hourtash et al. |
| 2017/0309069 A1 | 10/2017 | Thomas et al. |
| 2017/0319289 A1 | 11/2017 | Neff |
| 2017/0360493 A1 | 12/2017 | Zucher et al. |
| 2018/0014892 A1 | 1/2018 | Piron et al. |
| 2018/0049825 A1 | 2/2018 | Kwon et al. |
| 2018/0049826 A1 | 2/2018 | Fischer et al. |
| 2018/0049839 A1 | 2/2018 | Seong et al. |
| 2018/0056527 A1 | 3/2018 | Farritor et al. |
| 2018/0071029 A1 | 3/2018 | Srimohanarajeh et al. |
| 2018/0116742 A1 | 5/2018 | Dell et al. |
| 2018/0132965 A1 | 5/2018 | Nahum et al. |
| 2018/0153408 A1 | 6/2018 | Yao et al. |
| 2018/0185112 A1 | 7/2018 | Gowda et al. |
| 2018/0199900 A1 | 7/2018 | Mikemi et al. |
| 2018/0271511 A1 | 9/2018 | Stanton |
| 2018/0368656 A1 | 12/2018 | Austin et al. |
| 2019/0000567 A1 | 1/2019 | Allen et al. |
| 2019/0008598 A1 | 1/2019 | Frimer et al. |
| 2019/0021686 A1 | 1/2019 | Ogura |
| 2019/0125452 A1* | 5/2019 | Loke .................. A61B 17/1703 |
| 2019/0225195 A1 | 7/2019 | Shirouzu et al. |

FOREIGN PATENT DOCUMENTS

| | | |
|---|---|---|
| CN | 101883535 A | 11/2010 |
| CN | 101938952 A | 1/2011 |
| CN | 103750895 A | 4/2014 |
| CN | 104411258 A | 3/2015 |
| JP | 2012-500031 A | 1/2012 |

* cited by examiner

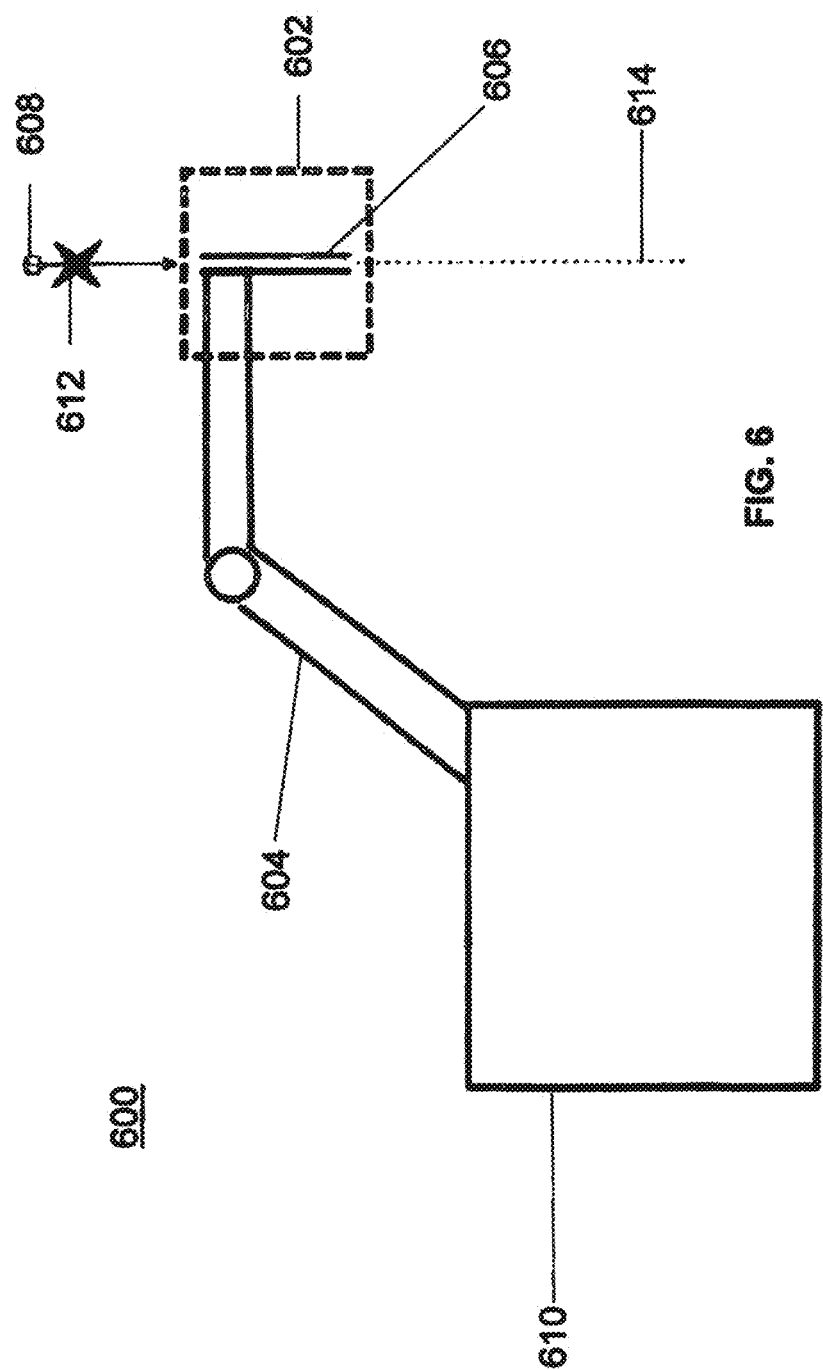

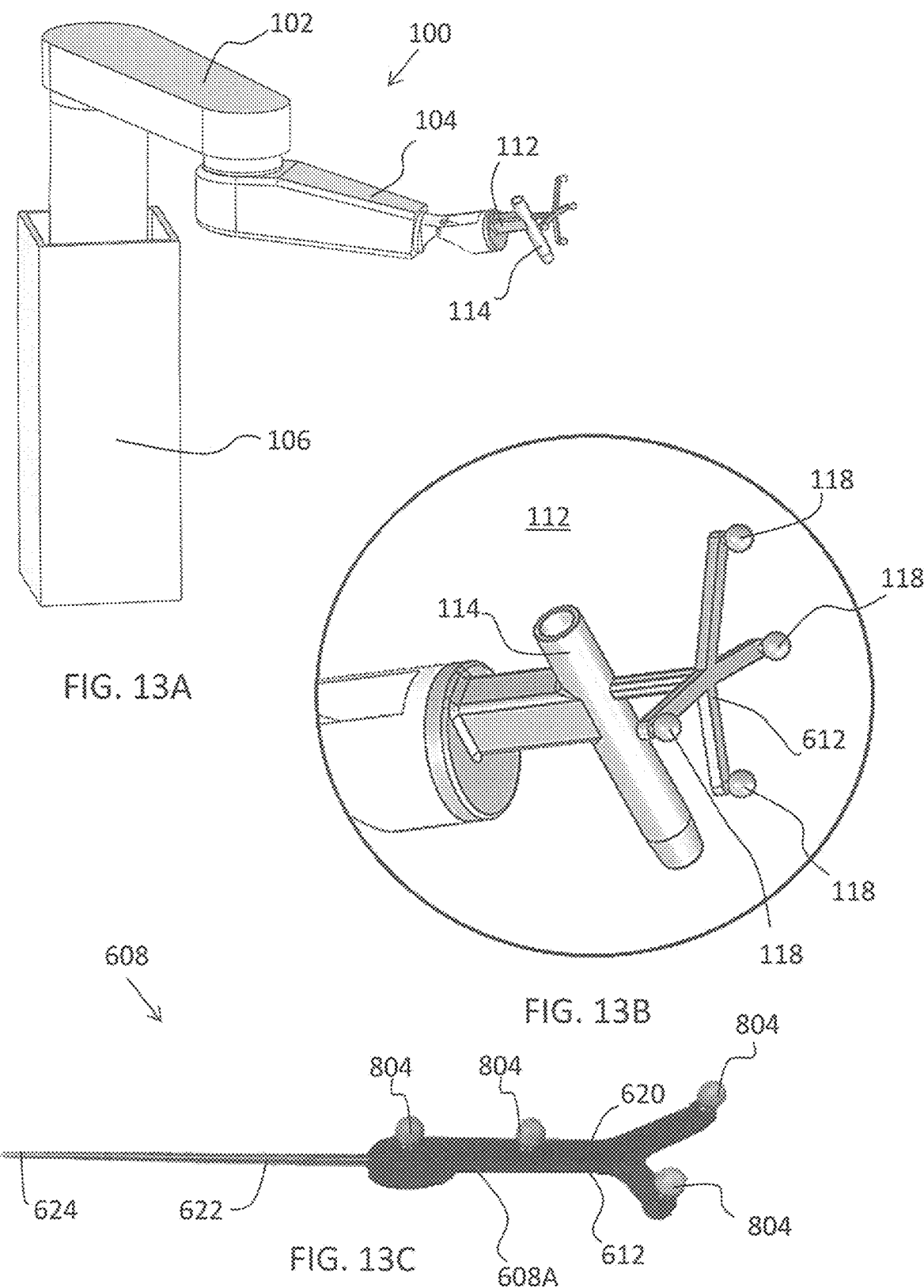

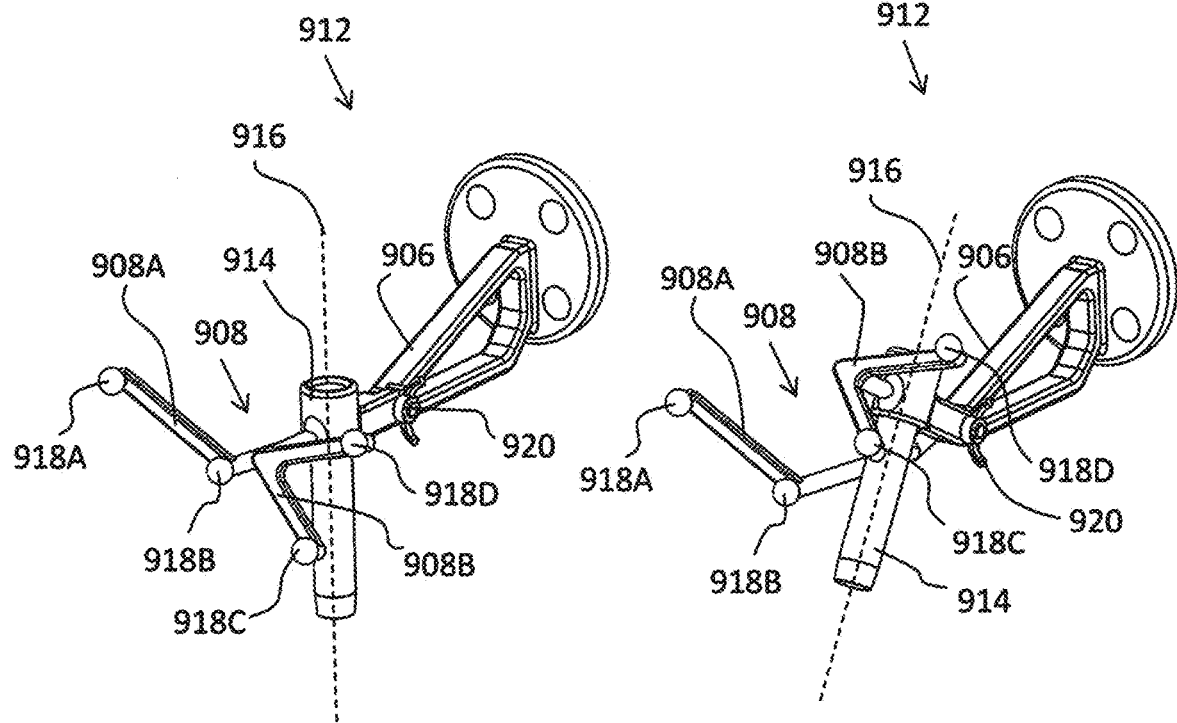
FIG. 14A  FIG. 14B
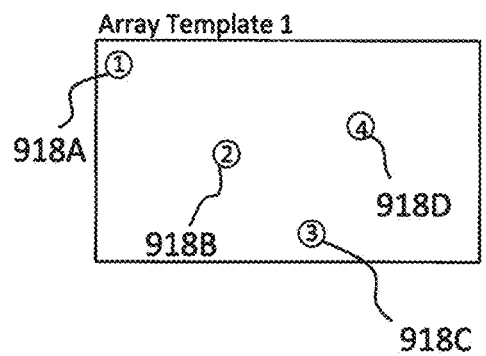
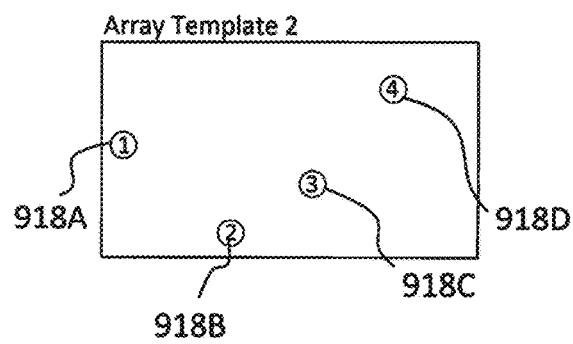
FIG. 14C  FIG. 14D

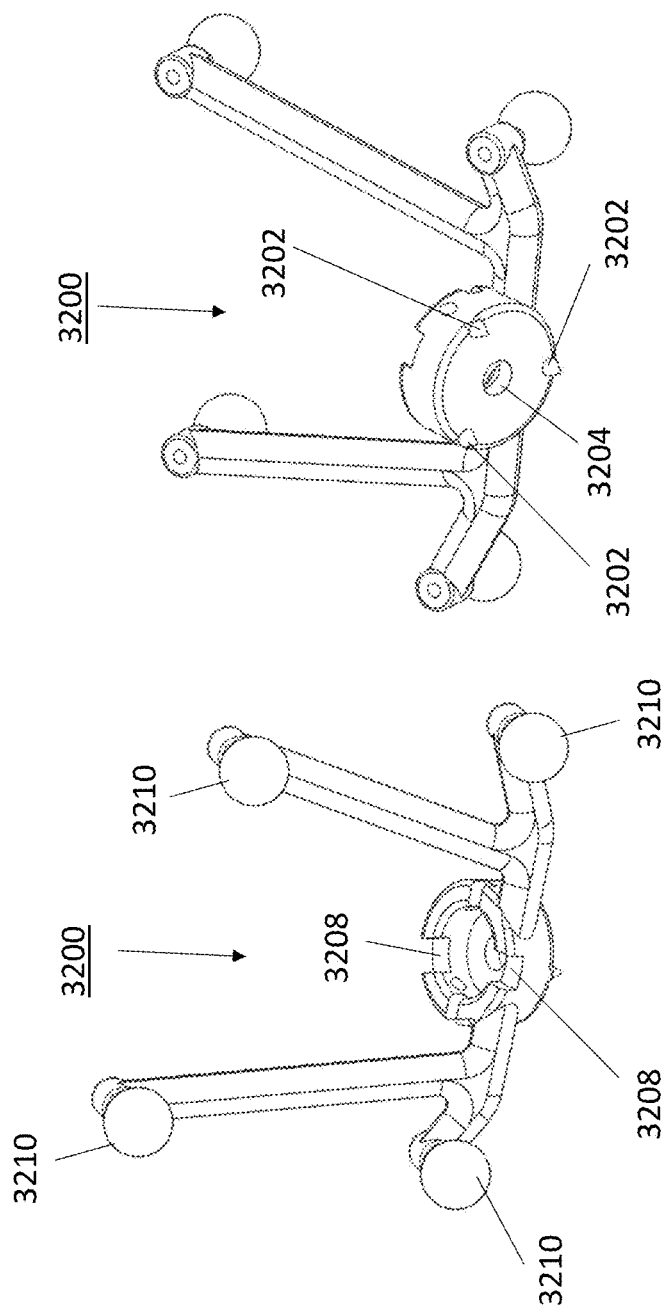

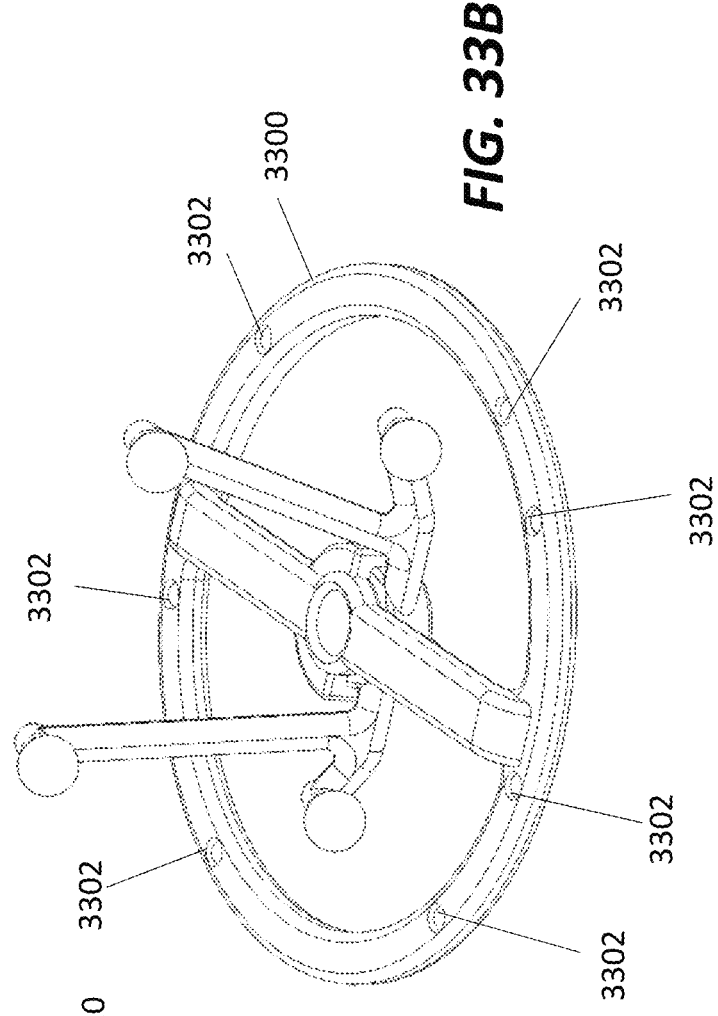
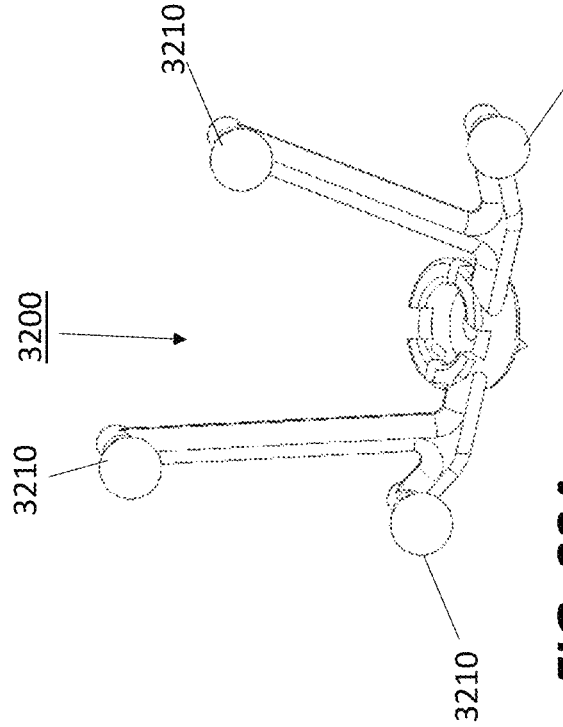

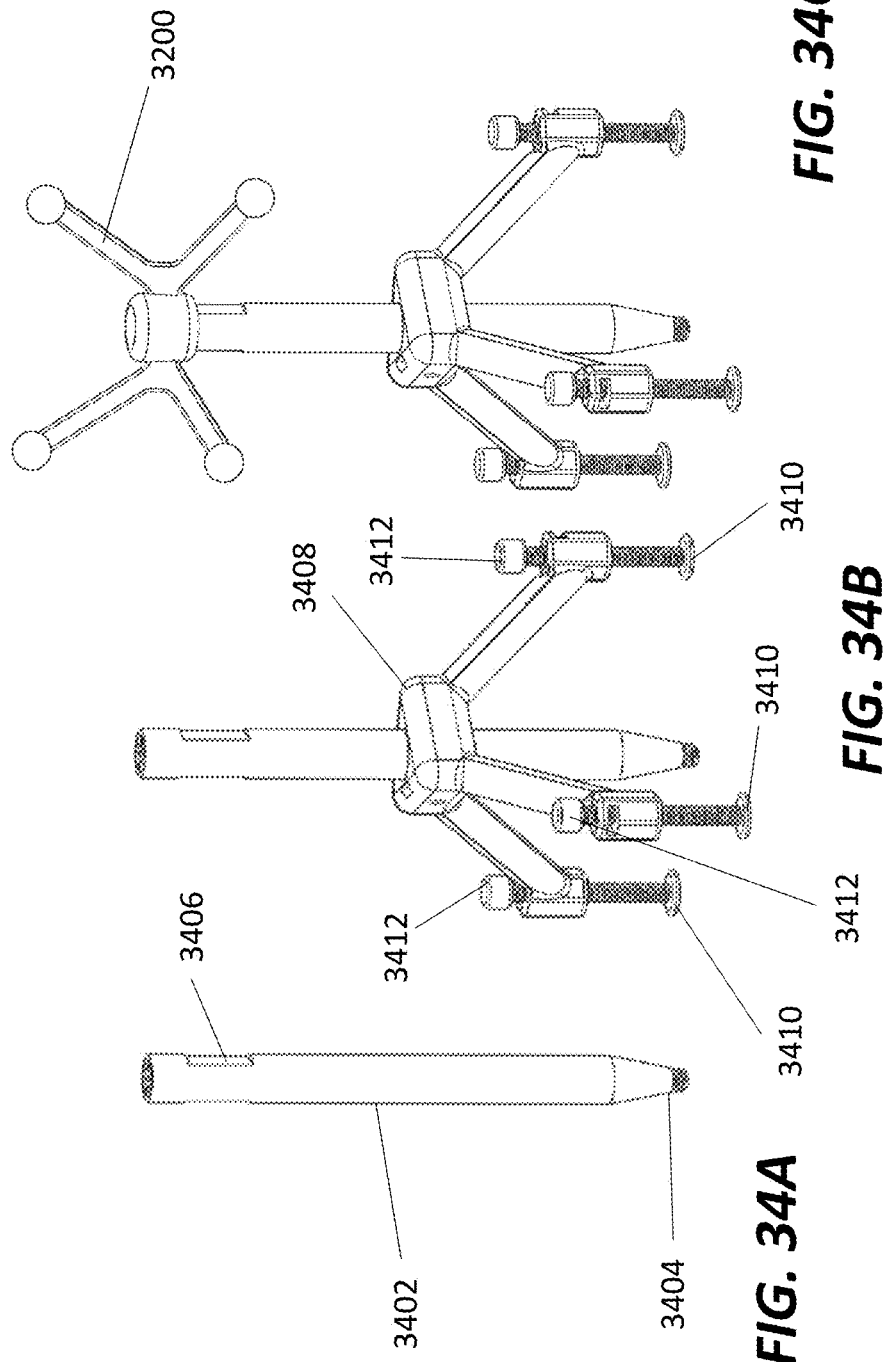

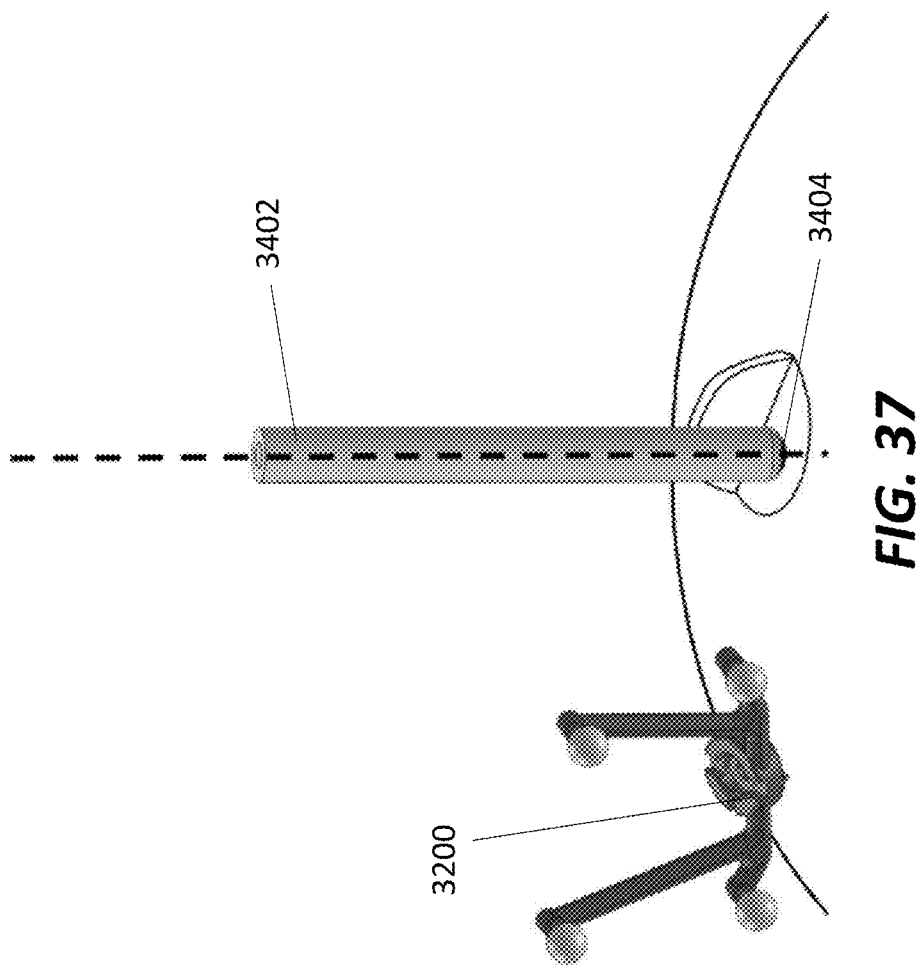

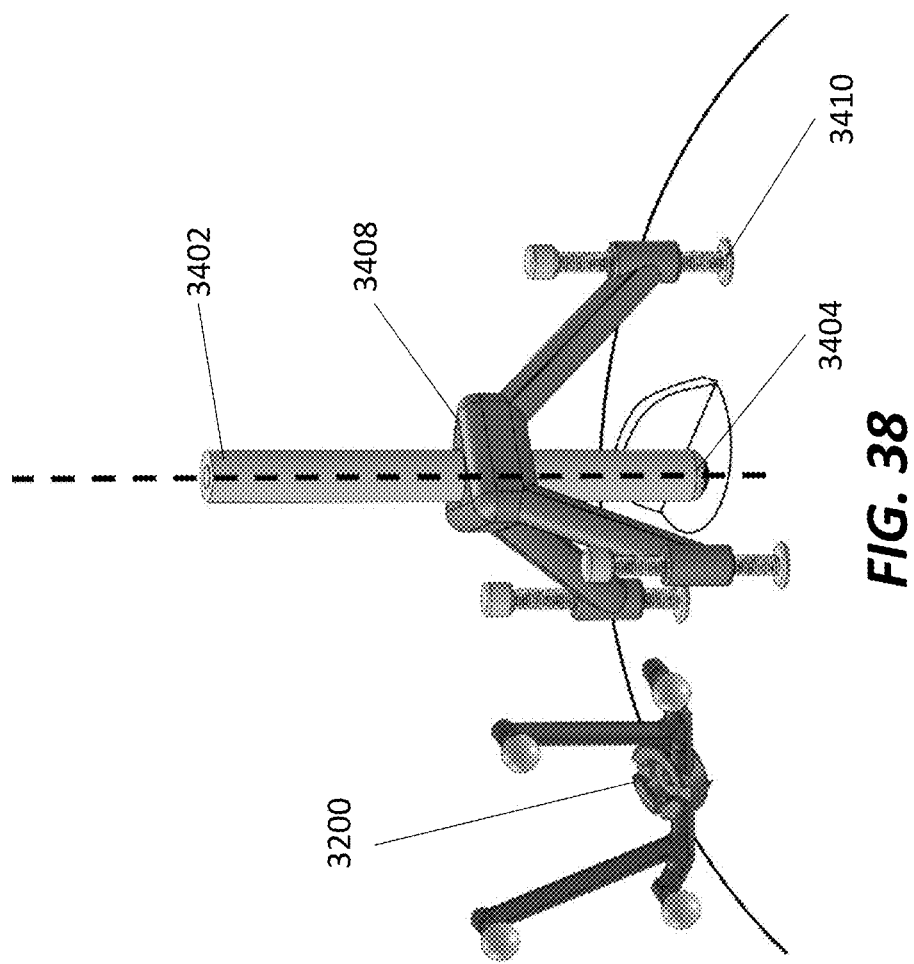

DRILL GUIDE FIXTURES, CRANIAL INSERTION FIXTURES, AND RELATED METHODS AND ROBOTIC SYSTEMS

CROSS-REFERENCE TO RELATED APPLICATIONS

This Patent Application is a continuation of U.S. application Ser. No. 16/535,223, filed Aug. 8, 2019, which is a continuation-in-part of U.S. application Ser. No. 16/209,266, filed Dec. 4, 2018, which is incorporated in its entirety herein for all purposes.

FIELD

The present disclosure relates to medical devices, and more particularly, medical devices for cranial procedures related methods and robotic systems.

BACKGROUND

For image-guided insertion of a needle or electrode into the brain, the surgeon may first secure a metal frame to the patient's skull using three or more pins. This frame is then automatically registered to the brain anatomy by taking a CT scan of the skull and frame and automatically detecting locations of fiducials on the frame within the scan, thereby allowing transformation between the coordinate system of the scan and the coordinate system of the frame. After the surgeon plans the desired trajectories into the brain on the CT images (typically with enhanced visualization from co-registered MR images), a multiaxial mechanical arc mechanism that has been calibrated to the frame's coordinate system is adjusted to hold a guide tube at the appropriate position relative to the skull and aligned with the planned trajectory. The surgeon then inserts the needle through this guide tube. Since the guide tube is interconnected to the skull via the mechanical arc and the frame, there may be a reduced chance during insertion of the needle that the patient might move relative to the guide tube, even if the patient is bumped, breathes, coughs, etc.

A possible robot-guided alternative may be to register a tracking camera to a robot and to an array on the patient's skull, then for the robot to automatically position a guide tube held by its end-effector next to the skull in line with the desired trajectory. The surgeon would then insert a needle through the robot-held guide tube. In such a method, however, sudden movement of the patient could lead to relative movement of the needle and the brain. For example, if the patient were to voluntarily or involuntarily contract muscles or cough, a rapid jerking movement of the patient could occur. Since the robot is rigidly mounted to the floor, the robot's guide tube may remain stationary relative to the patient, and if the needle was within the guide tube and the brain simultaneously, the needle could slice brain tissue laterally. If during needle insertion, the robot is actively and continuously adjusting its position through optical or force feedback, it may be possible for the robot to quickly reposition the guide tube so that it remains stationary relative to the brain even during such movement, but currently available feedback/response times may be insufficient to track such rapid movements, and the feedback path (e.g., line of sight for optical tracking) may need to remain unimpaired throughout the procedure.

SUMMARY

According to some embodiments of inventive concepts, a surgical robot system for attaching an electrode holder to a skull of a patient is described, the electrode holder configured to receive an electrode to be inserted into a brain of the patient. The surgical robot system includes a robot base comprising a computer, a robot arm coupled to the robot base, an end effector configured to be coupled to the robot arm, a guide tube having a detachable electrode holder disposed at a distal tip of the guide tip and a tracking array disposed near a proximal end of the guide tube, the guide tube configured to couple to the end effector, and a tripod mechanism configured to slide over the guide tube and allow fine adjustment of an angle of the guide tube relative to the skull.

According to some embodiments of inventive concepts, a method of using a surgical robot for attaching an electrode holder to a skull of a patient is described, the electrode holder configured to receive an electrode to be inserted into a brain of the patient. The method includes planning a trajectory, attaching an electrode holder to the skull using the surgical robot, and using the electrode holder for insertion of the electrode into the brain. The surgical robot includes a robot base comprising a computer, a robot arm coupled to the robot base, and an end effector configured to be coupled to the robot arm. The guide tube includes a detachable electrode holder disposed at a distal tip of the guide tip and a tracking array disposed near a proximal end of the guide tube, the guide tube configured to couple to the end effector, and a tripod mechanism configured to slide over the guide tube and allow adjustment of an angle of the guide tube relative to the skull. The method further includes positioning a dynamic reference base on the skull, positioning a temporary skirt fixture to the dynamic reference base, obtaining medical images of the dynamic reference base and temporary skirt feature, registering the dynamic reference base to the medical images using the temporary skirt fixture, removing the temporary skirt fixture, planning a trajectory of the electrode using the obtained medical images, using the robot to move the robot arm and end-effector to a desired location adjacent to the skull along the planned trajectory, using a drill to provide a hole in the skull while the robot guides the drill, providing the guide tube and electrode holder in the hole and removing the robot, lowering and locking the tripod mechanism to the guide tube, providing the tracking array to the guide tube and checking alignment of the guide relative to the planned trajectory, inserting an electrode into the guide tube and through the electrode holder; and removing the guide tube from the electrode holder.

DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 6 illustrates a surgical robot in accordance with an exemplary embodiment;

FIG. 13A illustrates a portion of a robot including the robot arm and an end-effector in accordance with an exemplary embodiment;

FIG. 13B is a close-up view of the end-effector, with a plurality of tracking markers rigidly affixed thereon, shown in FIG. 13A;

FIG. 13C is a tool or instrument with a plurality of tracking markers rigidly affixed thereon according to one embodiment;

FIG. 14A is an alternative version of an end-effector with moveable tracking markers in a first configuration;

FIG. 14B is the end-effector shown in FIG. 14A with the moveable tracking markers in a second configuration;

FIG. 14C shows the template of tracking markers in the first configuration from FIG. 14A;

FIG. 14D shows the template of tracking markers in the second configuration from FIG. 14B;

FIGS. 32A-32B illustrate different views of a dynamic reference array consistent with the principles of the present disclosure;

FIGS. 33A-33B illustrate a dynamic reference array without a temporary skirt fixture and with a temporary skirt fixture, respectively, consistent with the principles of the present disclosure;

FIGS. 34A, 34B and 34C illustrates a guide tube and detachable electrode holder consistent with the principles of the present disclosure;

FIG. 37 illustrates a dynamic reference array and a guide tube with a detachable electrode holder consistent with the principles of the present disclosure;

FIG. 38 illustrates a dynamic reference array, a guide tube with a detachable electrode holder, and tripod mechanism consistent with the principles of the present disclosure;

DETAILED DESCRIPTION

Figure 1:
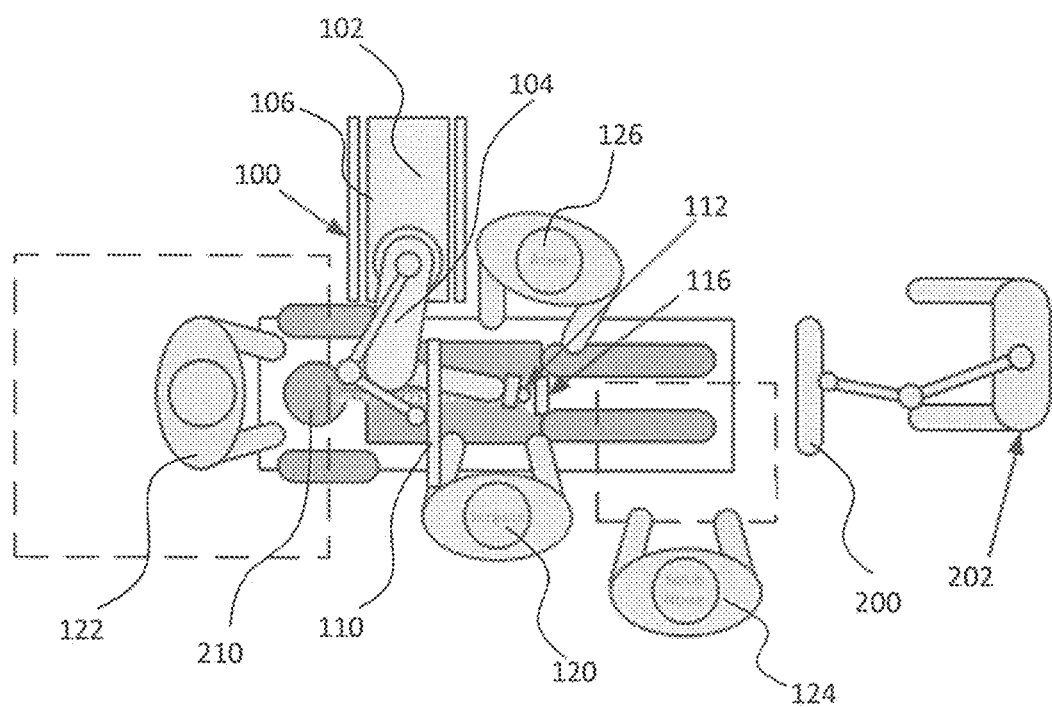
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
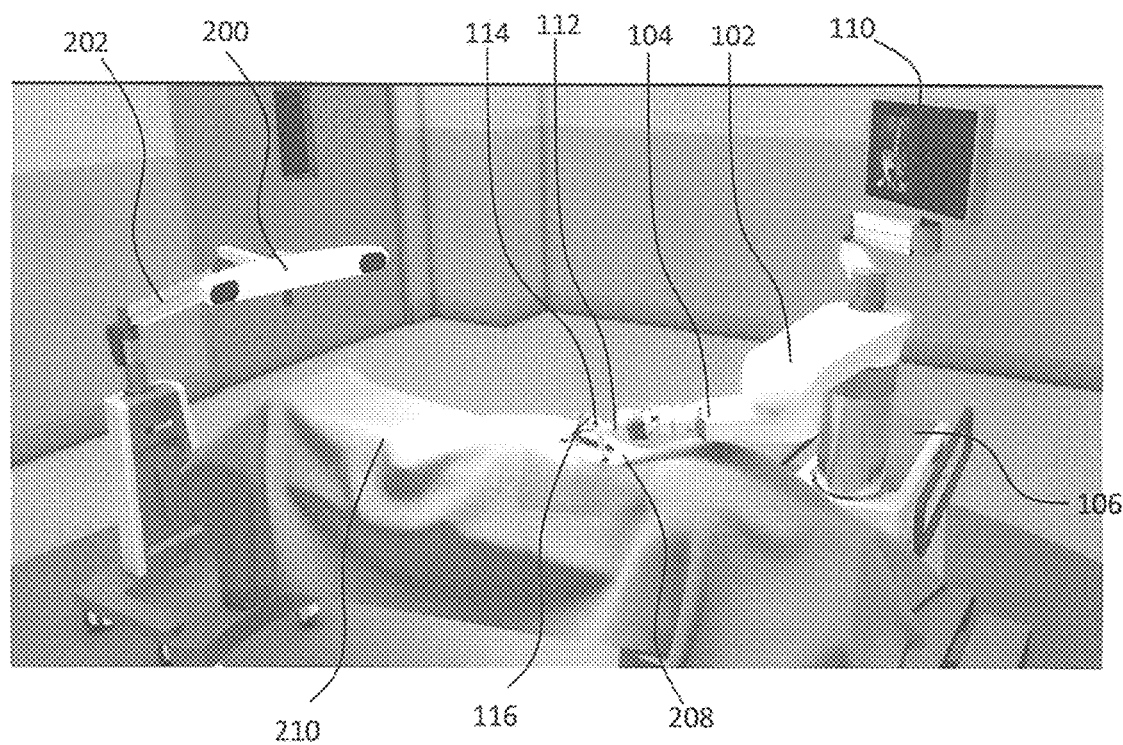
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to a bone of the patient 210). The surgical robot system 100 may also use a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 (shown as part of patient tracking device 116 in FIG. 2 and shown by enlarged view in FIGS. 13A-13B) in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and/or passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, and/or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

The markers 118 may include radiopaque or optical markers. The markers 118 may be suitably shaped include spherical, spheroid, cylindrical, cube, cuboid, or the like. In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in U.S. patent publication No. 2016/0242849, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
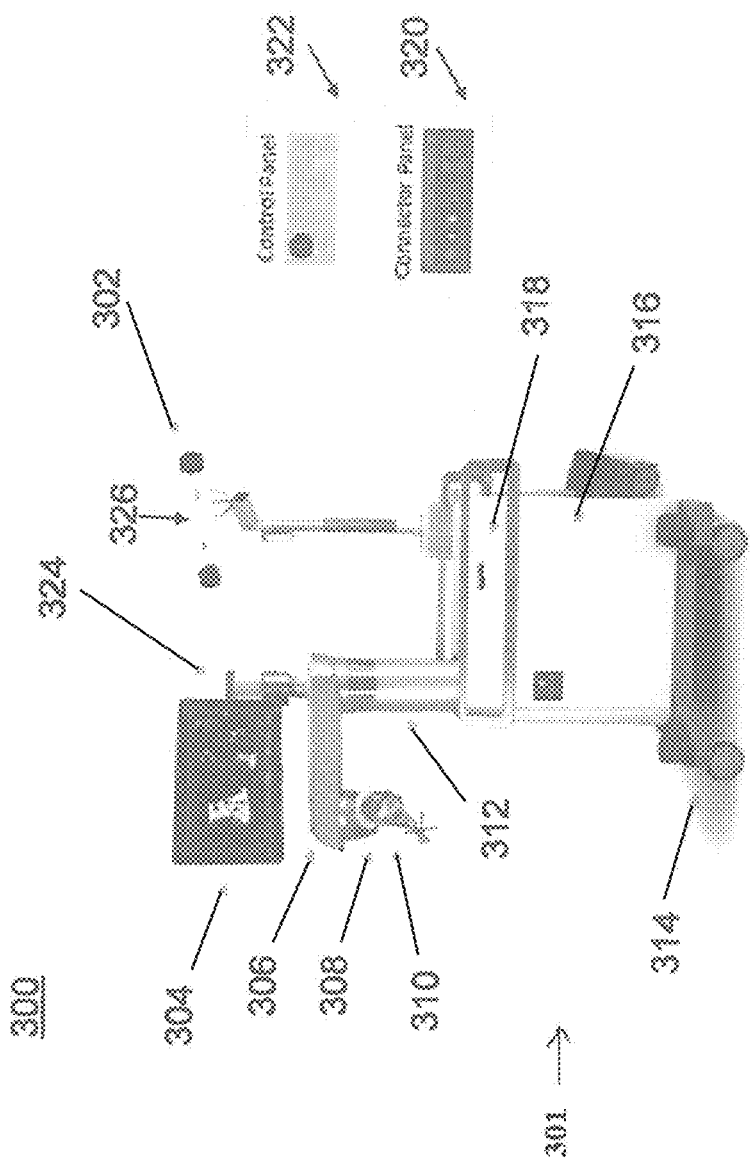
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
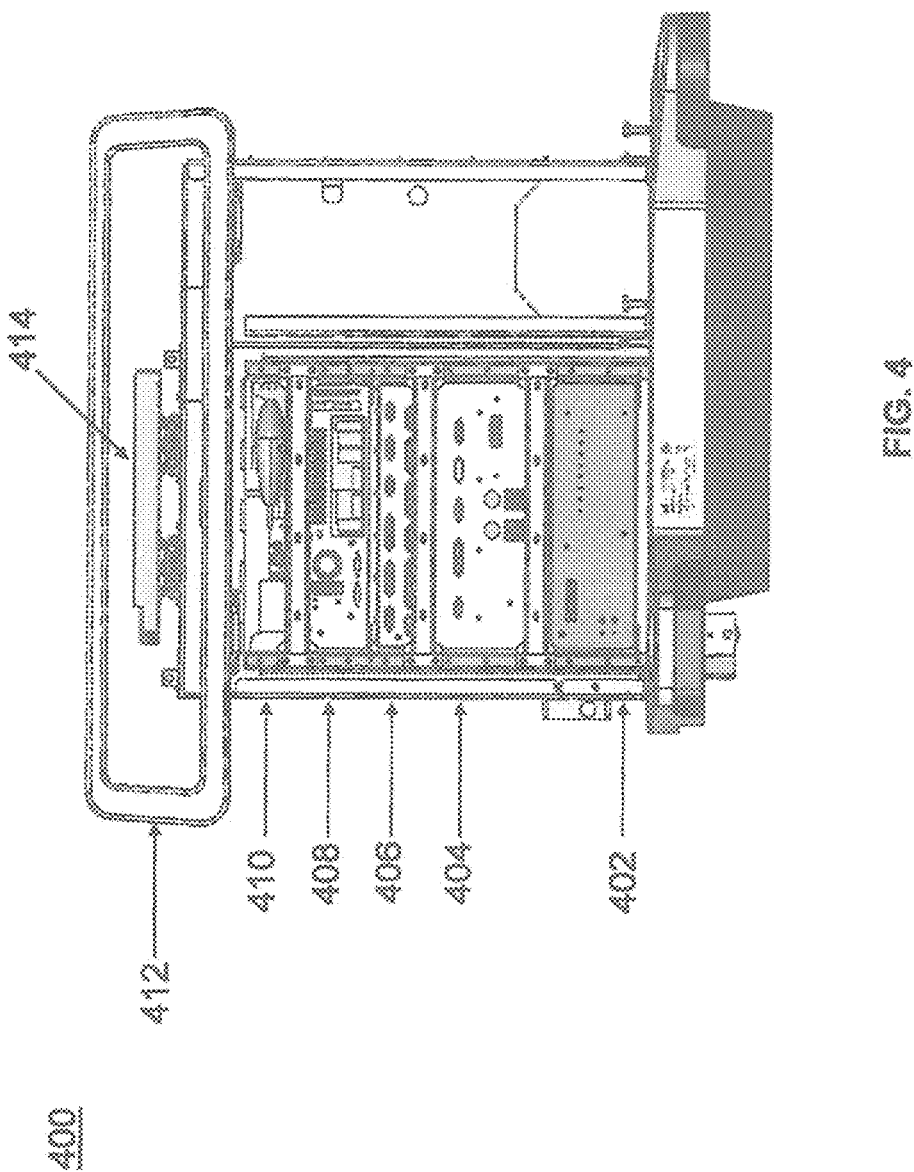
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
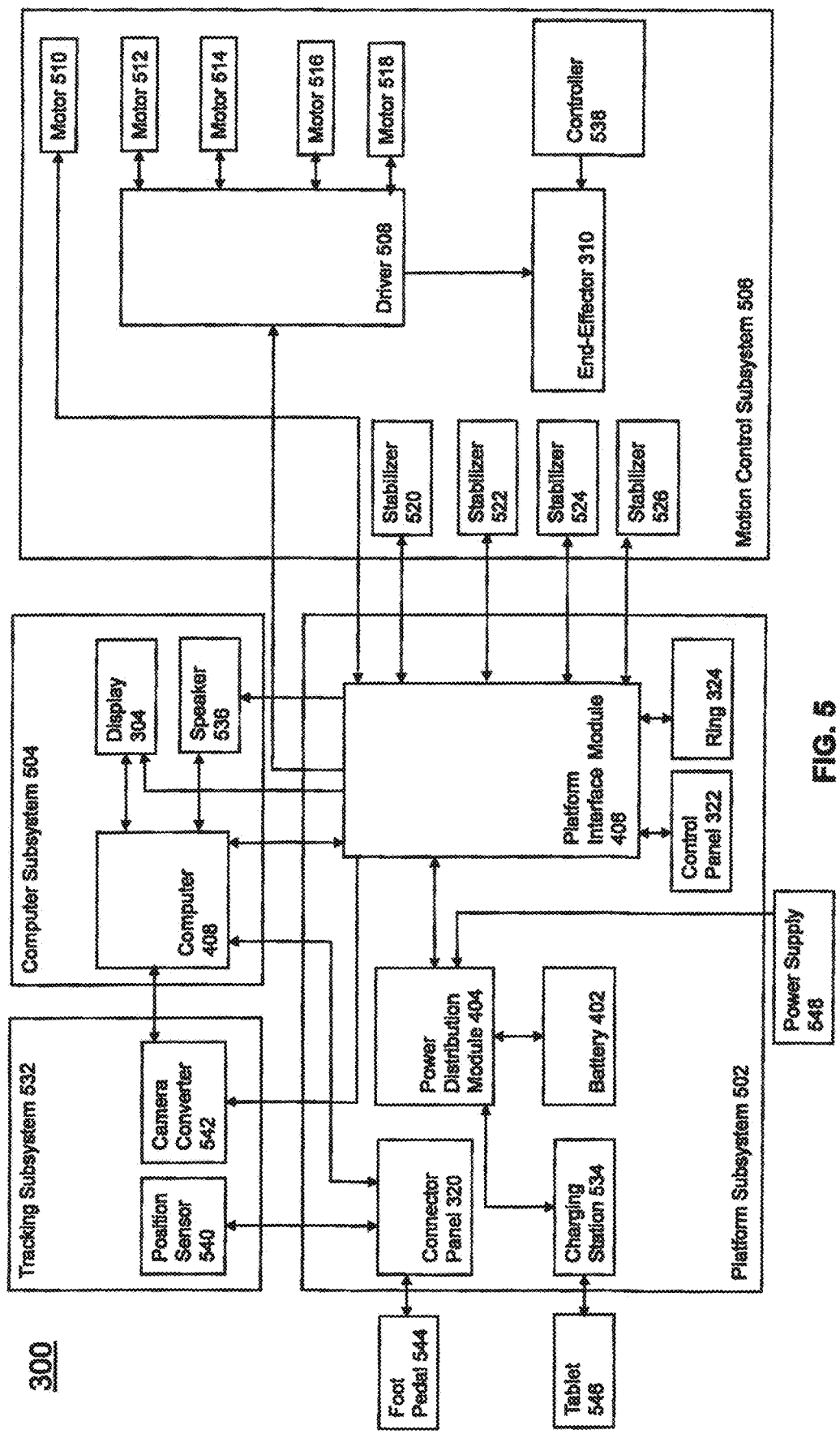
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on a three dimensional image of the patient's anatomy on display 304. The user may initiate this automatic movement by stepping on foot pedal 544 or some other input means.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
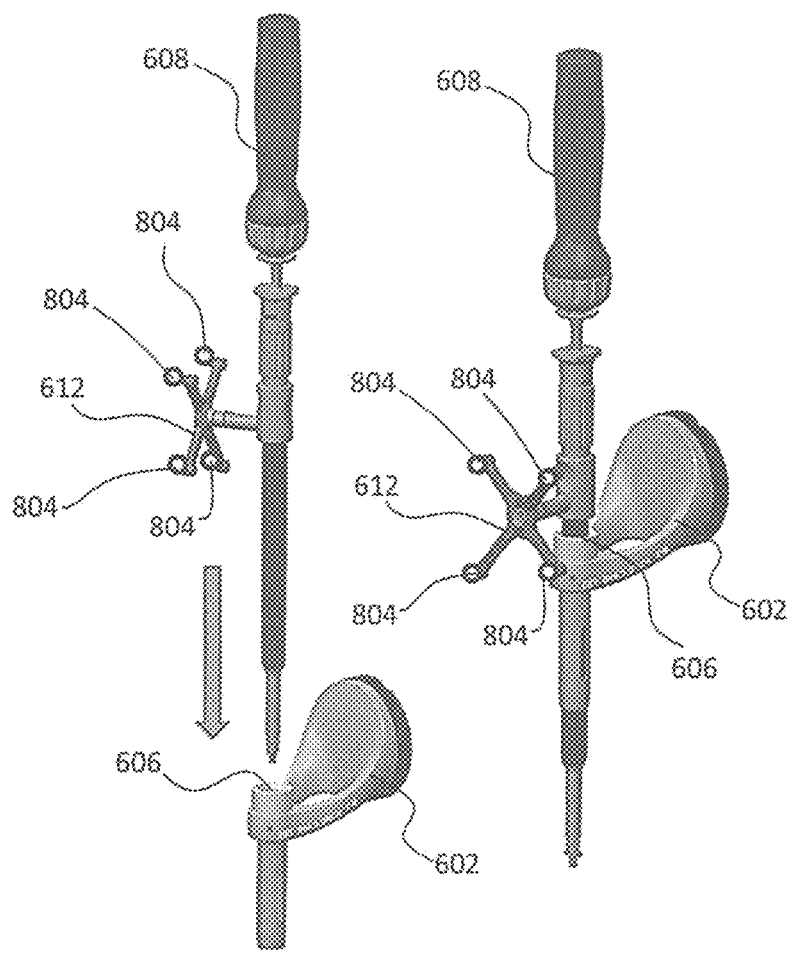
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

Figure 7A:
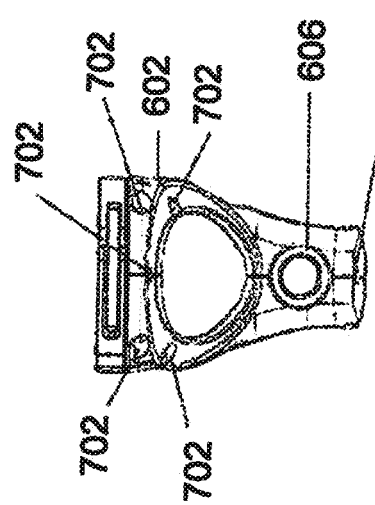
FIGS. 7A-7C illustrate an end-effector in accordance with an exemplary embodiment.
Figure 7B:
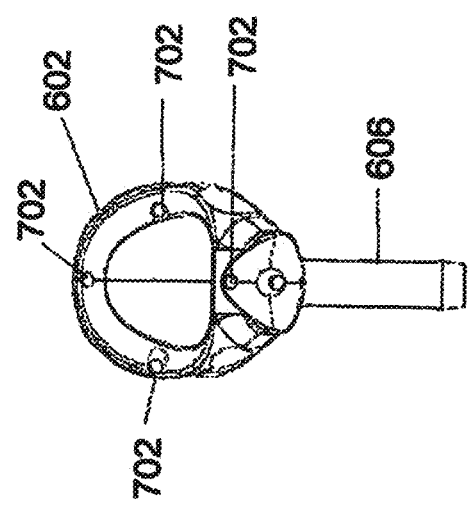
Figure 7C:
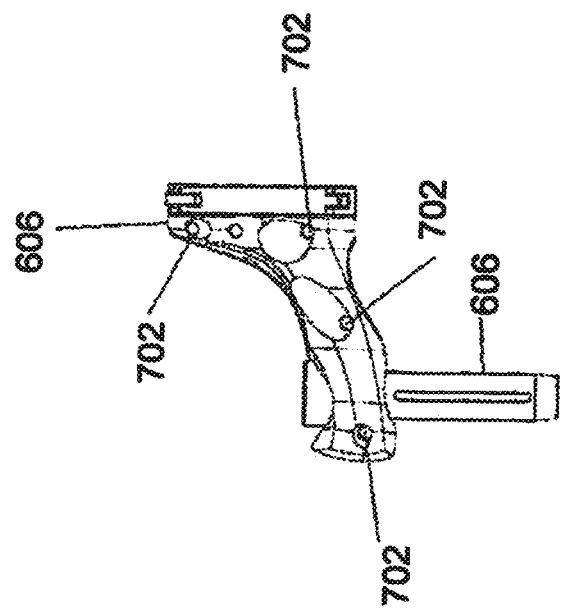

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
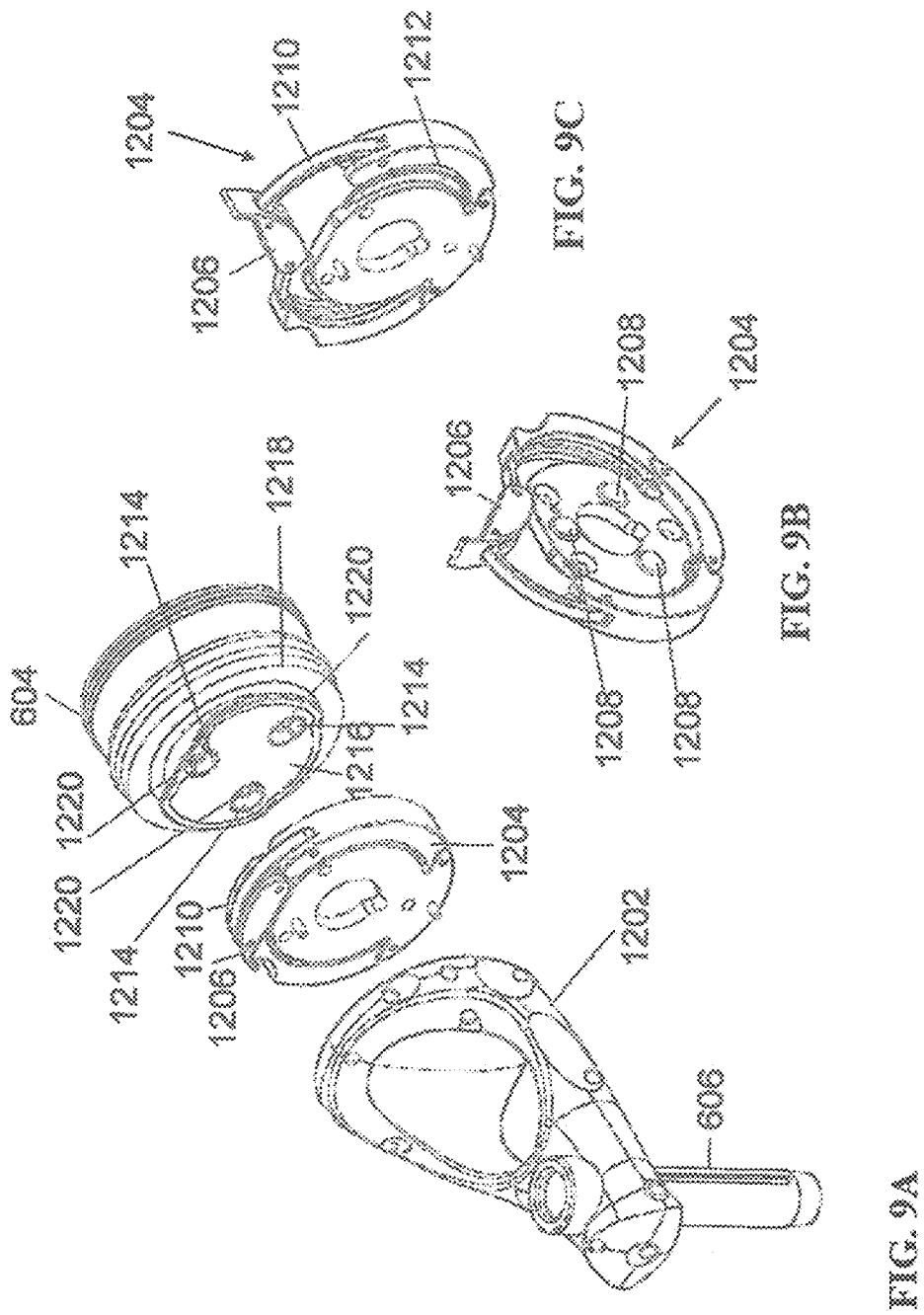
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (poly-ether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
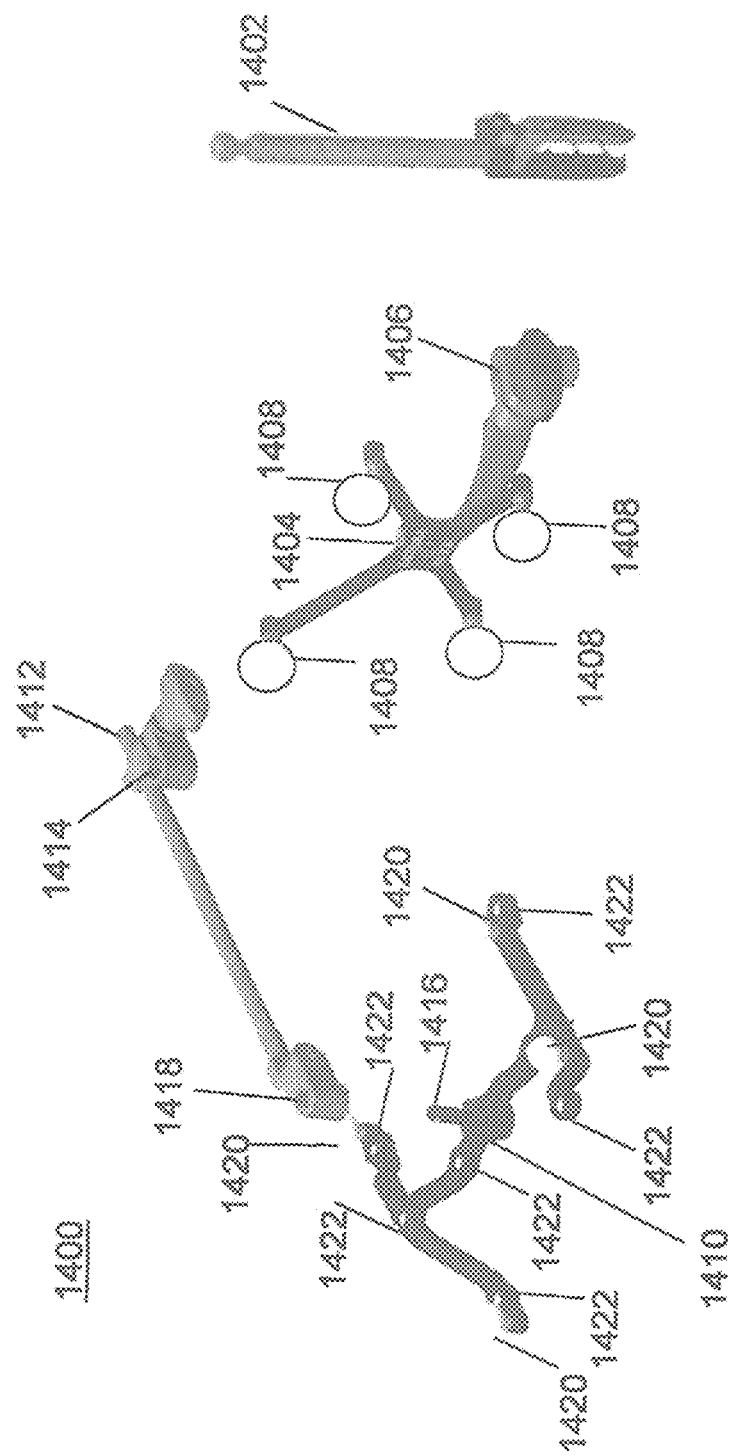
FIG. 10 illustrates a dynamic reference array, an imaging array, and other components in accordance with an exemplary embodiment.
Figure 11:
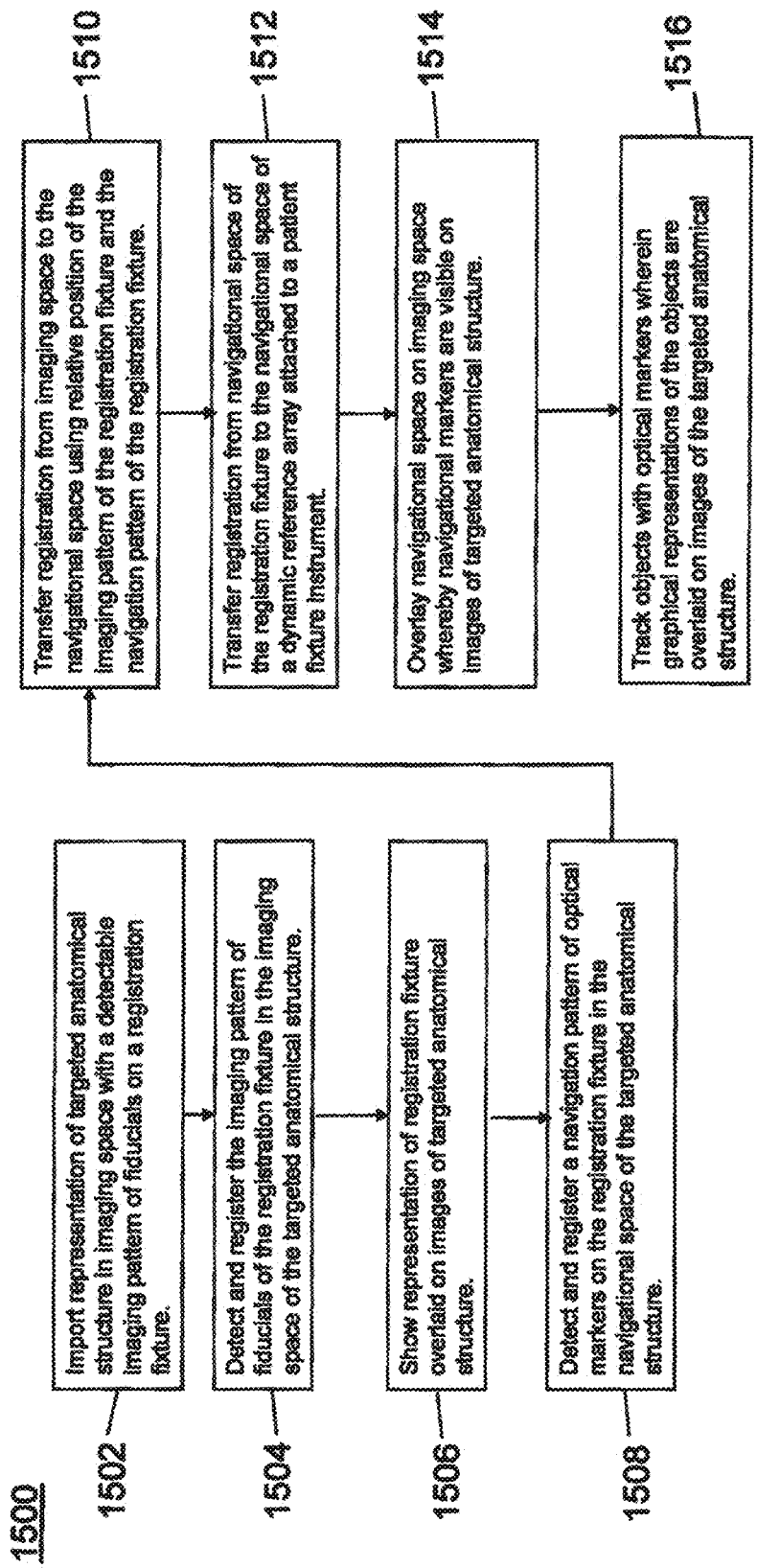
FIG. 11 illustrates a method of registration in accordance with an exemplary embodiment.

Referring to FIGS. 10 and 11, prior to or during a surgical procedure, certain registration procedures may be conducted to track objects and a target anatomical structure of the patient 210 both in a navigation space and an image space. To conduct such registration, a registration system 1400 may be used as illustrated in FIG. 10.

To track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
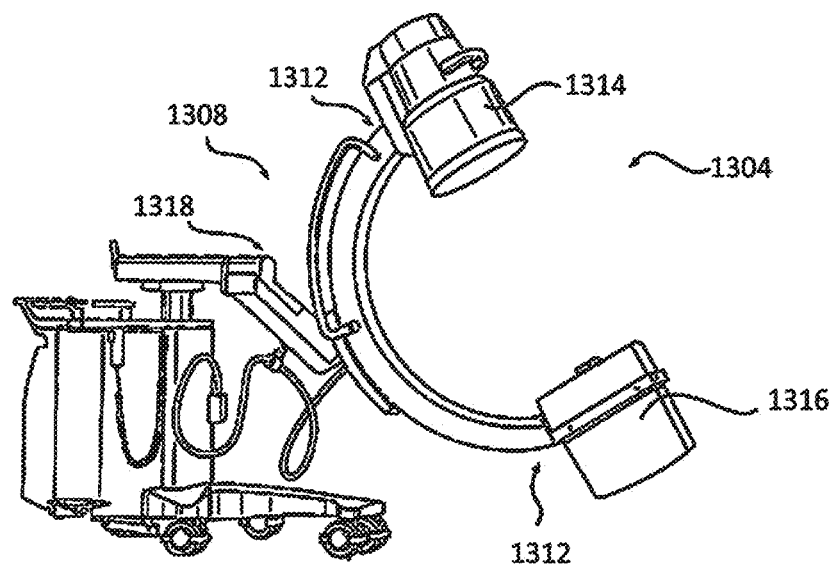
FIG. 12A-12B illustrate embodiments of imaging devices according to exemplary embodiments.
Figure 12B:
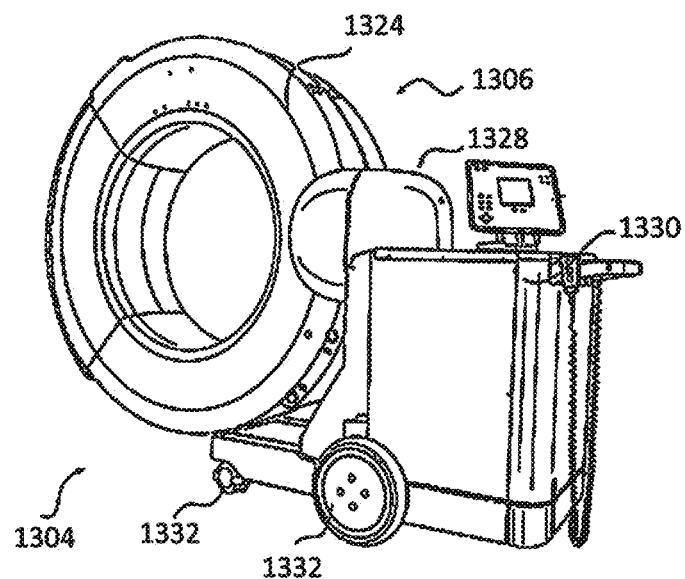

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screw driver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918 B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 13A and 13B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

Figure 15A:
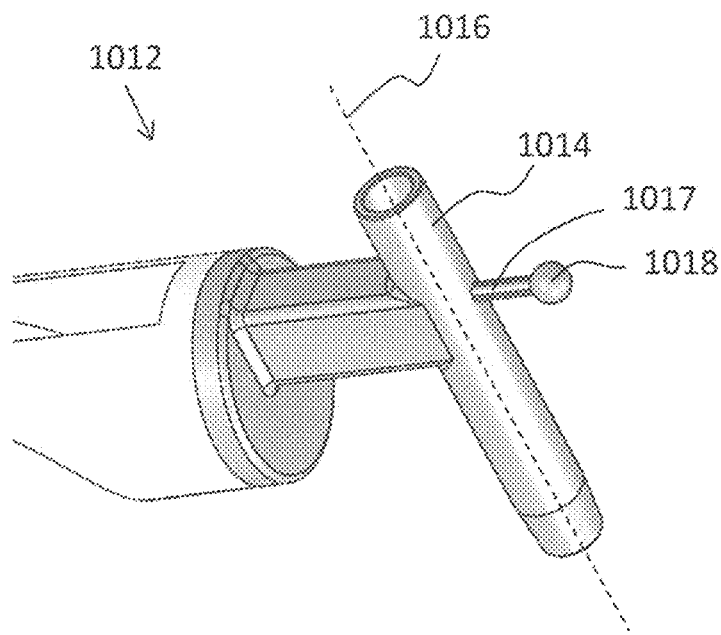
FIG. 15A shows an alternative version of the end-effector having only a single tracking marker affixed thereto.
Figure 15B:
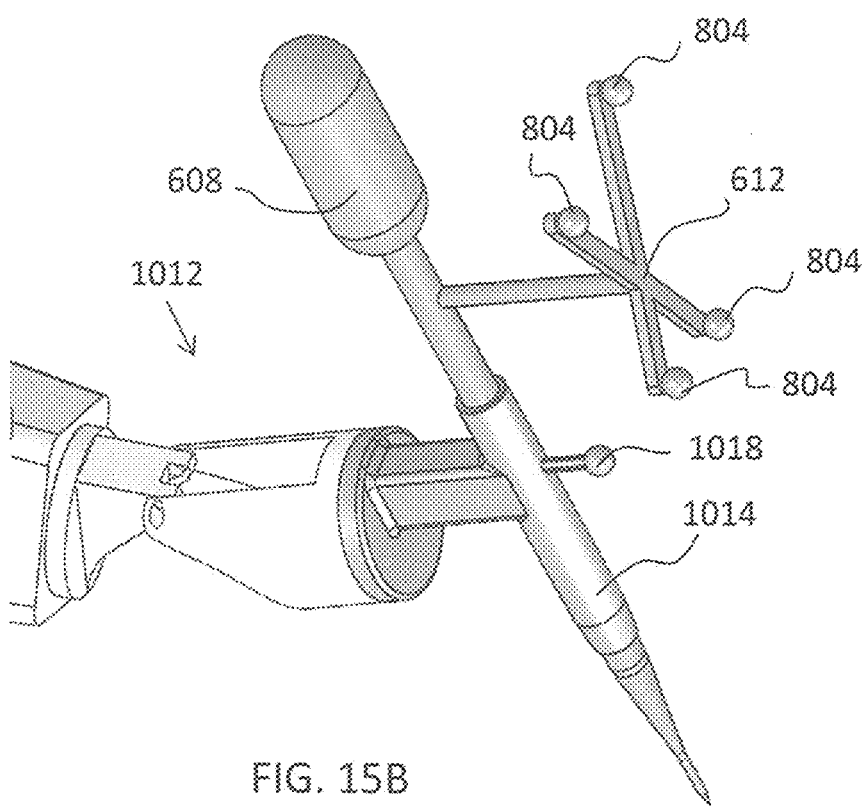
FIG. 15B shows the end-effector of FIG. 15A with an instrument disposed through the guide tube.

As shown in FIG. 15B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Figure 15C:
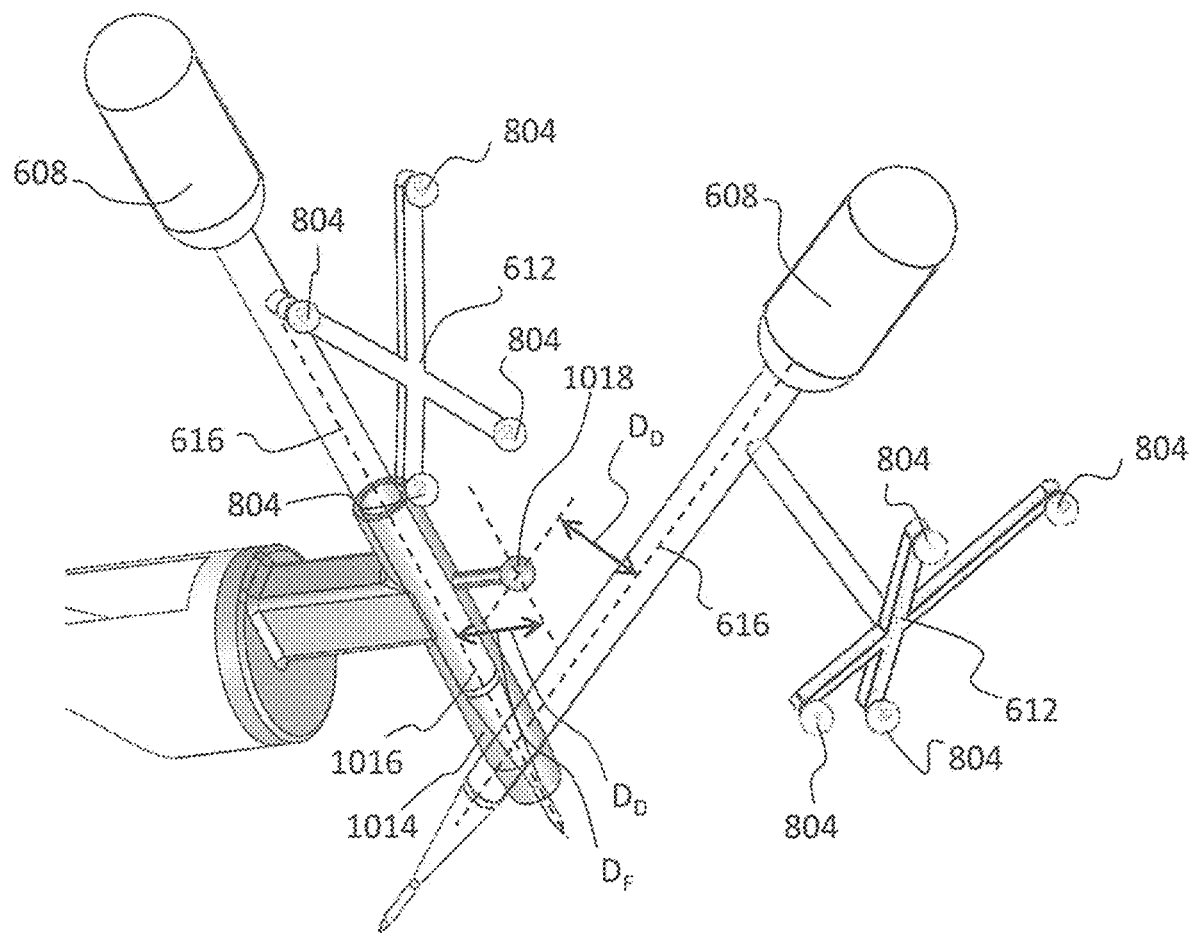
FIG. 15C shows the end-effector of FIG. 15A with the instrument in two different positions, and the resulting logic to determine if the instrument is positioned within the guide tube or outside of the guide tube.

Referring now to FIG. 15C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance DF from the single marker 1018 to the centerline or longitudinal axis 1016 of the guide tube 1014 is fixed and is known geometrically, and the position of the single marker 1018 can be tracked. Therefore, when a detected distance DD from tool centerline 616 to single marker 1018 matches the known fixed distance DF from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance DD matches the fixed distance DF. For example, in FIG. 15C, the normal detected distance DD from tool centerline 616 to the single marker 1018 matches the fixed distance DF from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Figure 15D:
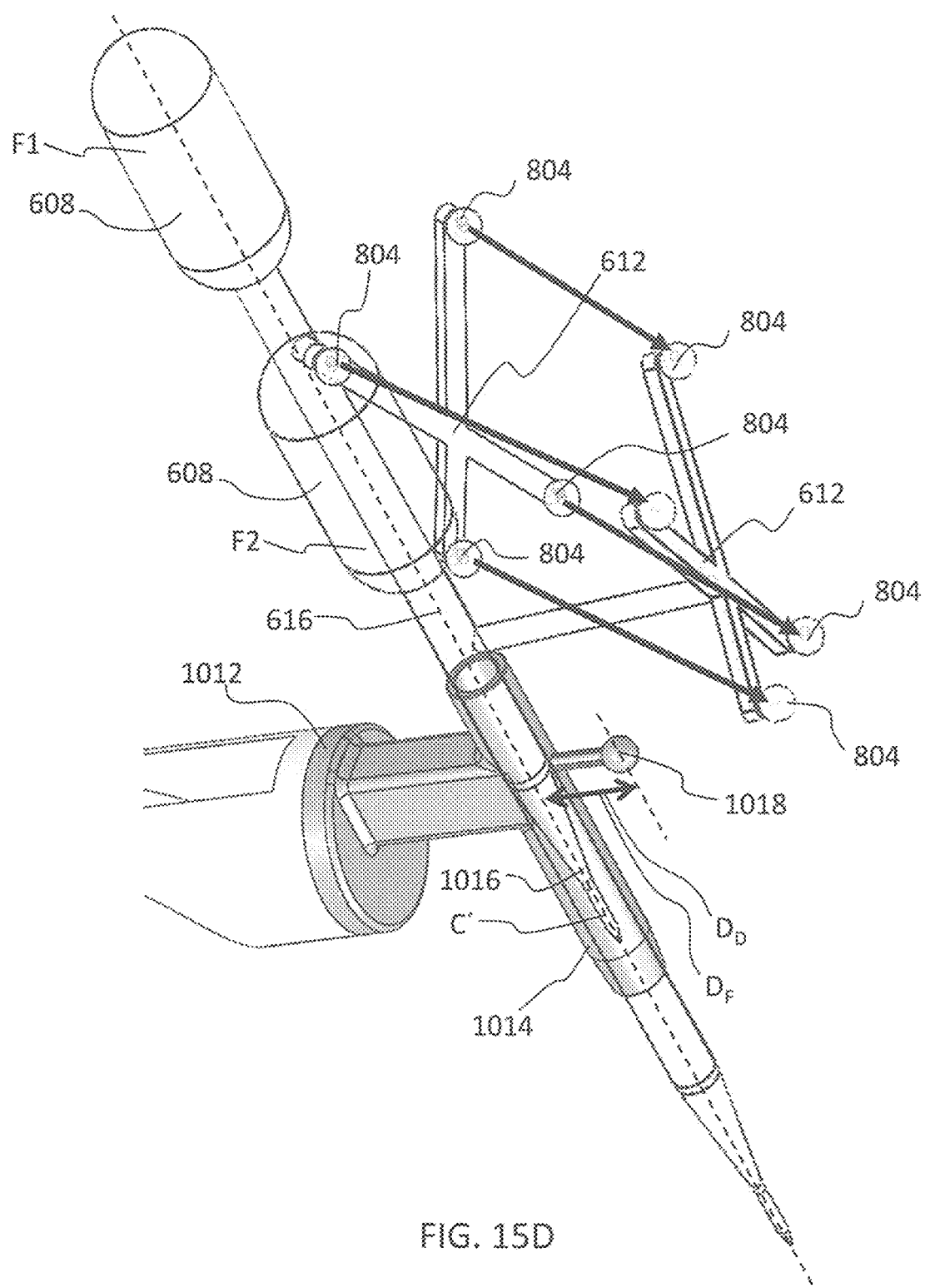
FIG. 15D shows the end-effector of FIG. 15A with the instrument in the guide tube at two different frames and its relative distance to the single tracking marker on the guide tube.

Turning now to FIG. 15D, programmed logic can be used to look for frames of tracking data in which the detected distance DD from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance DD from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

Figure 15E:
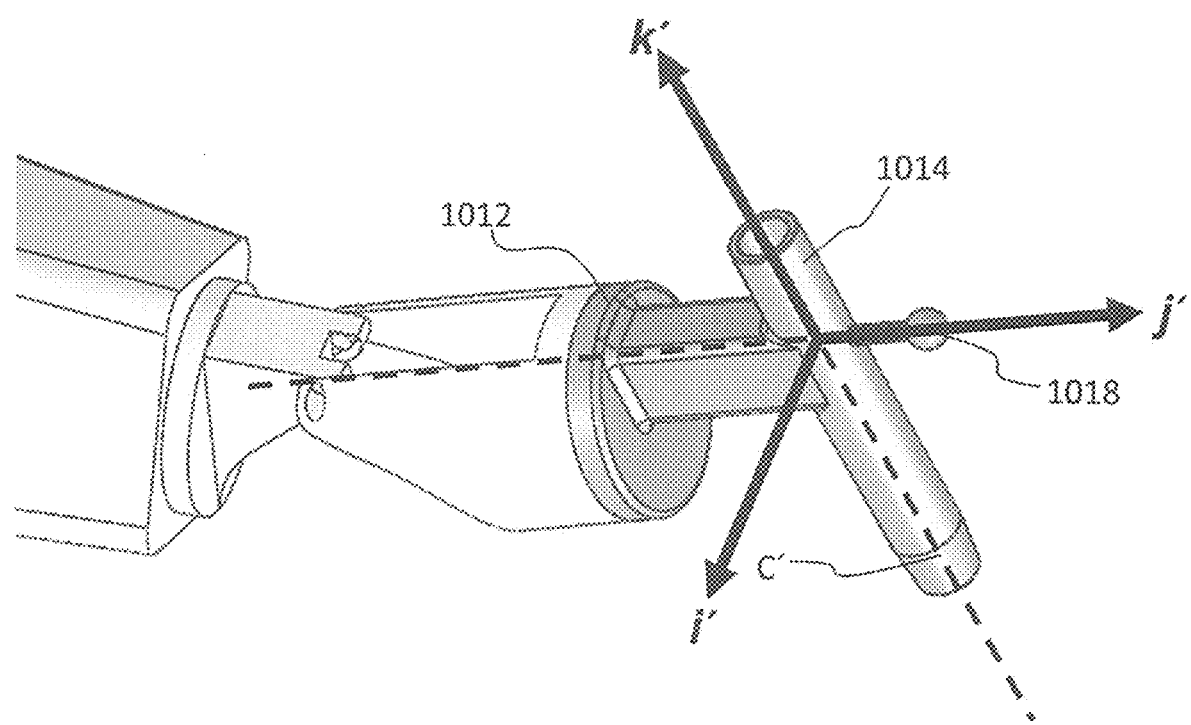
FIG. 15E shows the end-effector of FIG. 15A relative to a coordinate system.

With emphasis on FIG. 15E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 15E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

Figure 16:
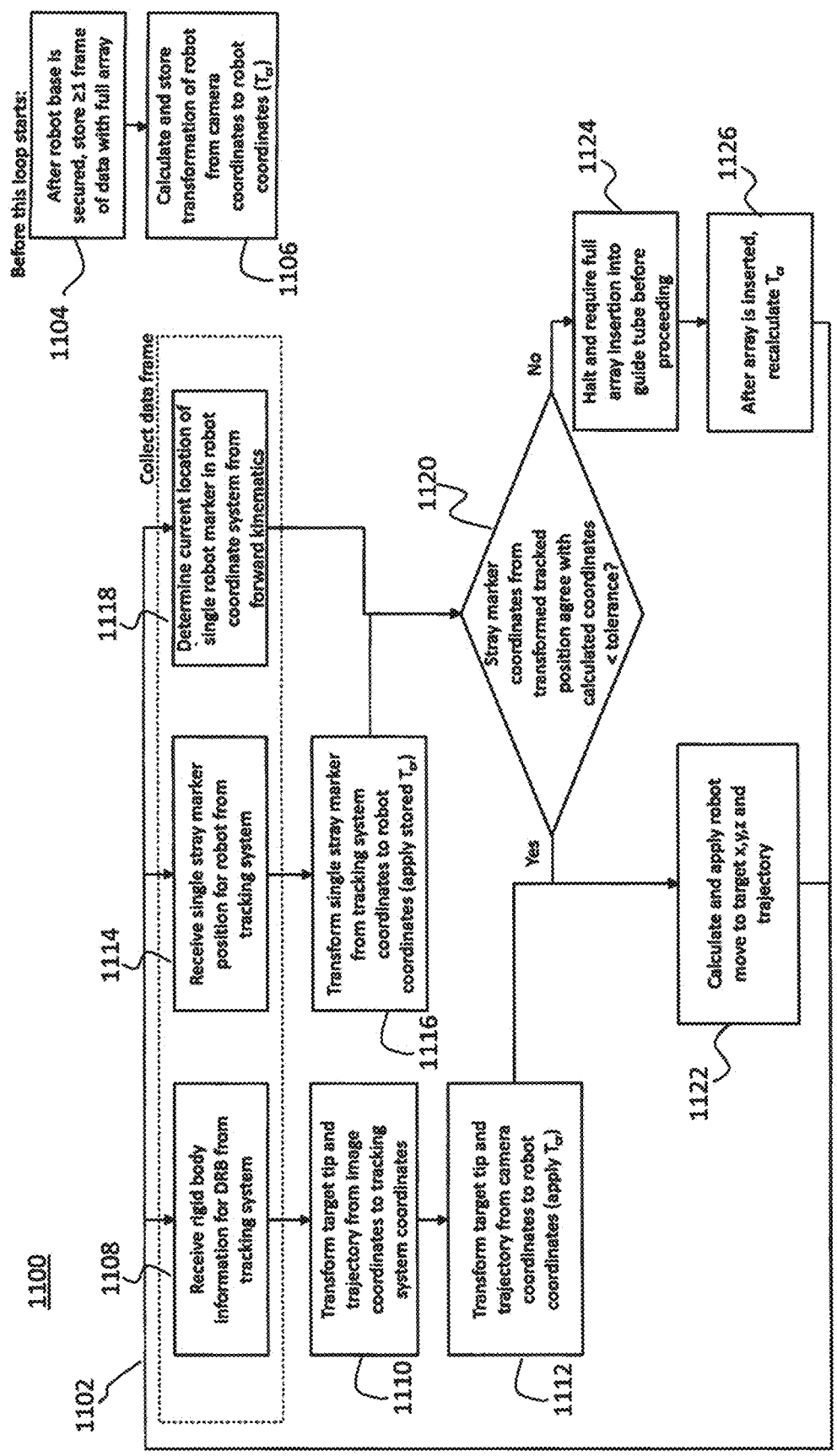
FIG. 16 is a block diagram of a method for navigating and moving the end-effector of the robot to a desired target trajectory.

FIG. 16 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS.

Figure 18A:
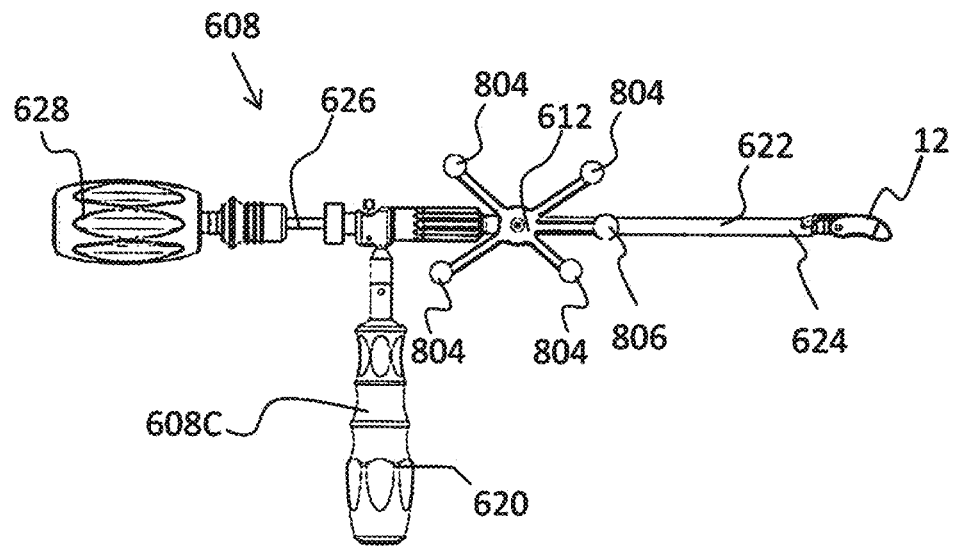
FIGS. 18A-18B depict an instrument for inserting an articulating implant having fixed and moveable tracking markers in insertion and angled positions, respectively.
Figure 18B:
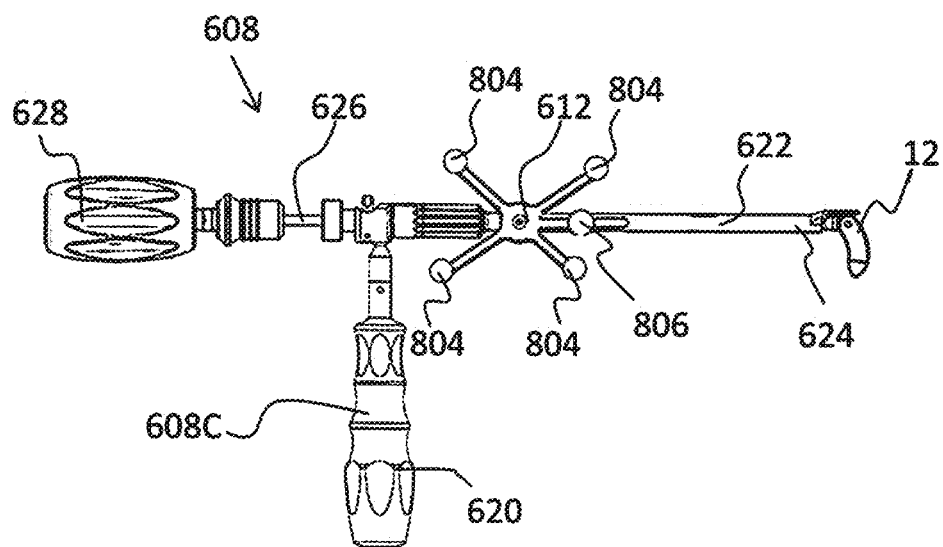

17A-17B or angle of an articulating interbody spacer shown in FIGS. 18A-18B). Thus, the system and/or the user can determine the height or angle of the implant 10, 12 based on the location of the moveable marker 806.

Figure 17A:
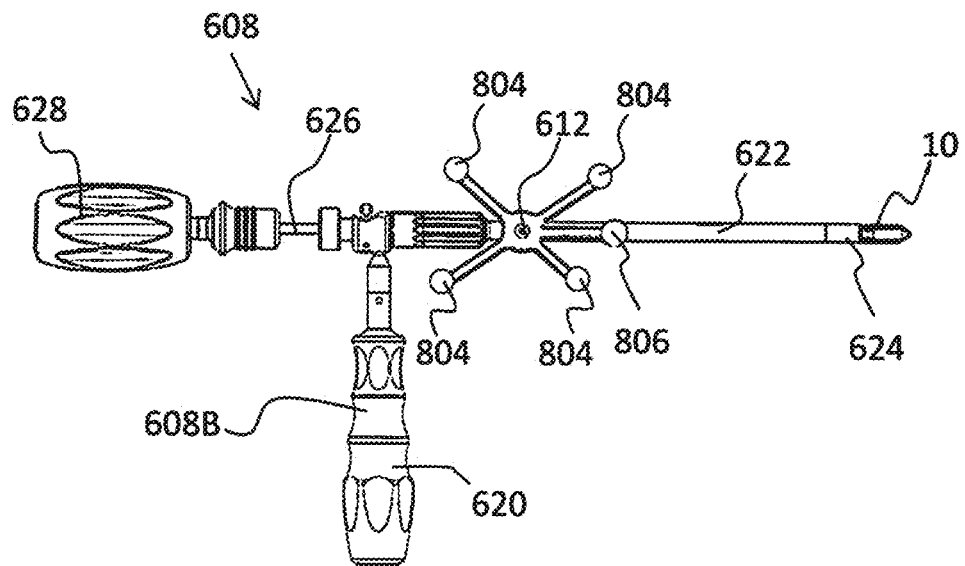
FIGS. 17A-17B depict an instrument for inserting an expandable implant having fixed and moveable tracking markers in contracted and expanded positions, respectively.
Figure 17B:
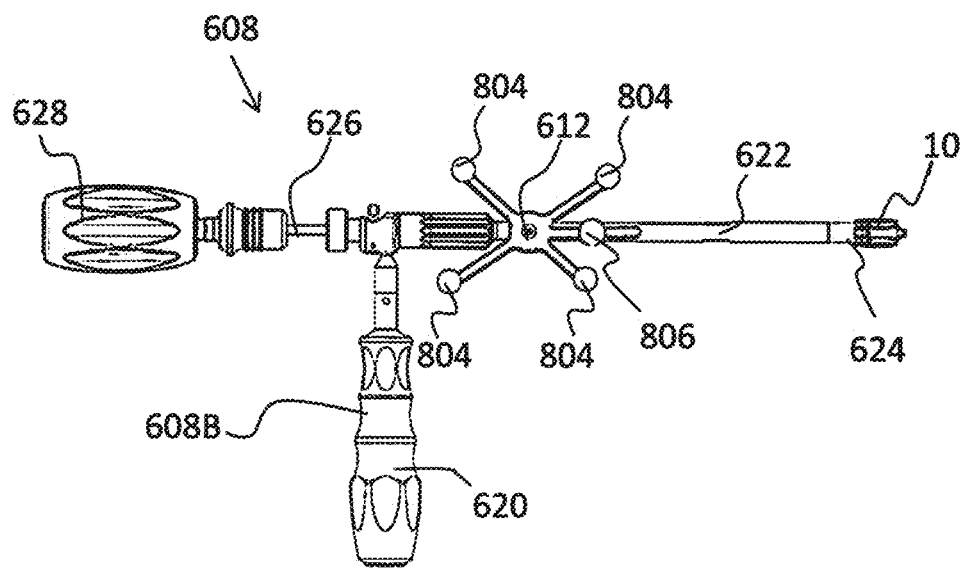

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the expandable spacer 10 at its initial height, and FIG. 17B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Turning now to FIGS. 18A-18B, four fixed markers 804 are used to define the implant holder 608C and a fifth, moveable marker 806 is configured to slide within a pre-determined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, cements, or the like.

Figure 19A:
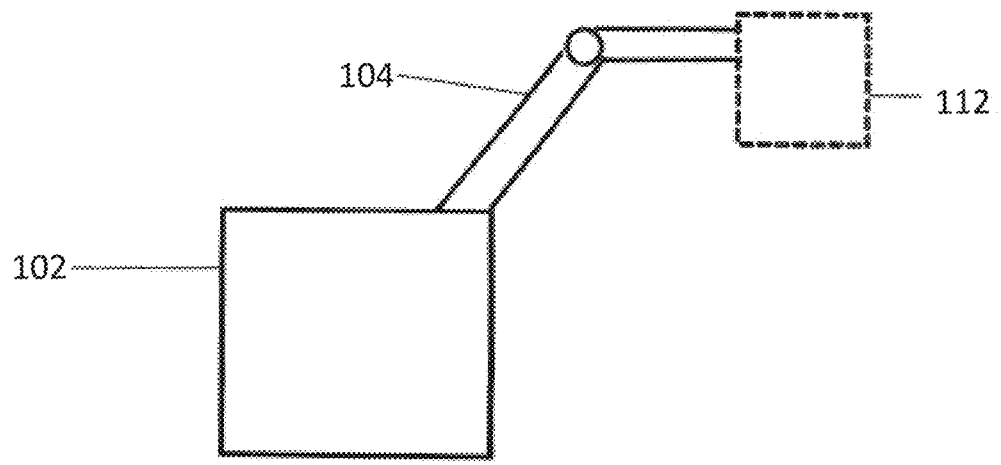
FIG. 19A depicts an embodiment of a robot with interchangeable or alternative end-effectors.

Turning now to FIG. 19A, it is envisioned that the robot end-effector 112 is interchangeable with other types of end-effectors 112. Moreover, it is contemplated that each end-effector 112 may be able to perform one or more functions based on a desired surgical procedure. For example, the end-effector 112 having a guide tube 114 may be used for guiding an instrument 608 as described herein. In addition, end-effector 112 may be replaced with a different or alternative end-effector 112 that controls a surgical device, instrument, or implant, for example.

The alternative end-effector 112 may include one or more devices or instruments coupled to and controllable by the robot. By way of non-limiting example, the end-effector 112, as depicted in FIG. 19A, may comprise a retractor (for example, one or more retractors disclosed in U.S. Pat. Nos. 8,992,425 and 8,968,363) or one or more mechanisms for inserting or installing surgical devices such as expandable intervertebral fusion devices (such as expandable implants exemplified in U.S. Pat. Nos. 8,845,734; 9,510,954; and 9,456,903), stand-alone intervertebral fusion devices (such as implants exemplified in U.S. Pat. Nos. 9,364,343 and 9,480,579), expandable corpectomy devices (such as corpectomy implants exemplified in U.S. Pat. Nos. 9,393,128 and 9,173,747), articulating spacers (such as implants exemplified in U.S. Pat. No. 9,259,327), facet prostheses (such as devices exemplified in U.S. Pat. No. 9,539,031), laminoplasty devices (such as devices exemplified in U.S. Pat. No. 9,486,253), spinous process spacers (such as implants exemplified in U.S. Pat. No. 9,592,082), inflatables, fasteners including polyaxial screws, uniplanar screws, pedicle screws, posted screws, and the like, bone fixation plates, rod constructs and revision devices (such as devices exemplified in U.S. Pat. No. 8,882,803), artificial and natural discs, motion preserving devices and implants, spinal cord stimulators (such as devices exemplified in U.S. Pat. No. 9,440,076), and other surgical devices. The end-effector 112 may include one or instruments directly or indirectly coupled to the robot for providing bone cement, bone grafts, living cells, pharmaceuticals, or other deliverable to a surgical target. The end-effector 112 may also include one or more instruments designed for performing a discectomy, kyphoplasty, vertebrostenting, dilation, or other surgical procedure.

The end-effector itself and/or the implant, device, or instrument may include one or more markers 118 such that the location and position of the markers 118 may be identified in three-dimensions. It is contemplated that the markers 118 may include active or passive markers 118, as described herein, that may be directly or indirectly visible to the cameras 200. Thus, one or more markers 118 located on an implant 10, for example, may provide for tracking of the implant 10 before, during, and after implantation.

Figure 19B:
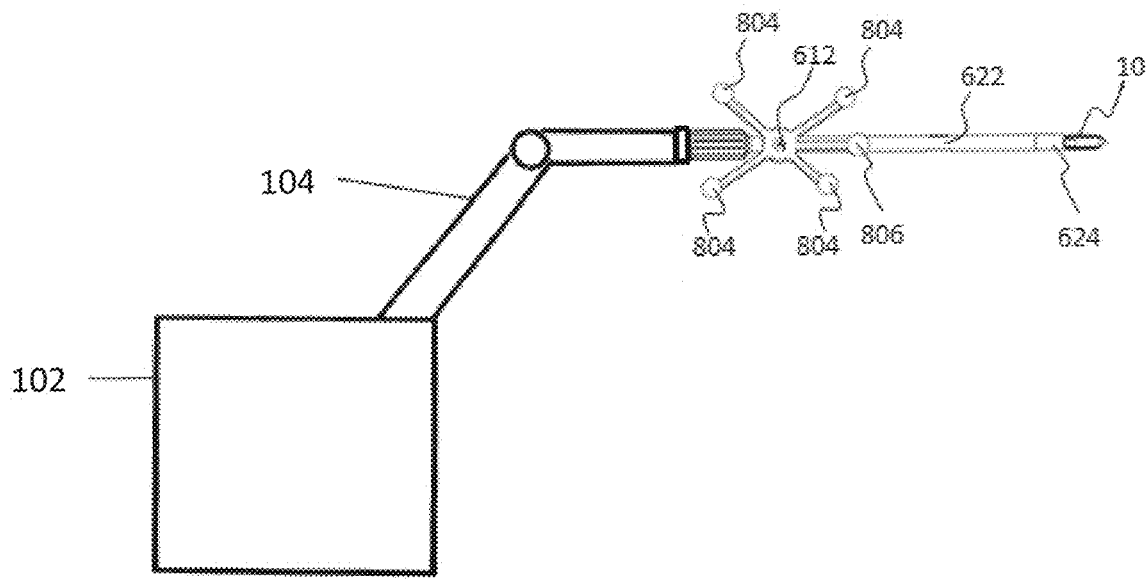
FIG. 19B depicts an embodiment of a robot with an instrument style end-effector coupled thereto.

As shown in FIG. 19B, the end-effector 112 may include an instrument 608 or portion thereof that is coupled to the robot arm 104 (for example, the instrument 608 may be coupled to the robot arm 104 by the coupling mechanism shown in FIGS. 9A-9C) and is controllable by the robot system 100. Thus, in the embodiment shown in FIG. 19B, the robot system 100 is able to insert implant 10 into a patient and expand or contract the expandable implant 10. Accordingly, the robot system 100 may be configured to assist a surgeon or to operate partially or completely independently thereof. Thus, it is envisioned that the robot system 100 may be capable of controlling each alternative end-effector 112 for its specified function or surgical procedure.

Although the robot and associated systems described herein are generally described with reference to spine applications, it is also contemplated that the robot system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures.

During robotic spine (or other) procedures, a Dynamic Reference Base (DRB) may thus be affixed to the patient (e.g., to a bone of the patient), and used to track the patient anatomy. Since the patient is breathing, a position of the DRB (which is attached to the patient's body) may oscillate. Once a surgical tool is robotically moved to a target trajectory and locked into position, patient movement (e.g., due to breathing) may cause deviation from the target trajectory even through the end-effector (e.g., surgical tool) is locked in place. This deviation/shift (if unnoticed and unaccounted for) may thus reduce accuracy of the system and/or surgical procedure.

During the process of inserting a needle or electrode into the brain under guidance, it may be important that the brain does not move (even slightly) relative to the guide tube used to guide insertion of the needle or electrode. Methods are disclosed herein to prepare the skull under robotic guidance and then to deliver a precise temporary needle guide fixture to mount to the skull using robotic guidance. Then, with the robot set aside, the needle is inserted with reference only to the temporary guide fixture. Since the temporary guide fixture is fixed relative to the skull, there should be reduced risk of brain injury should the patient move during needle insertion.

According to some embodiments, robotic guidance may be used to prepare the skull, and a temporary guide fixture (also referred to as a cranial insertion fixture) may be attached to the prepared skull. A needle (or other medical device) may then be inserted into the brain through the temporary guide fixture without further assistance from the robot. If the patient were to twitch during preparation of the skull or delivery or attachment of the temporary device, little/no damage to brain tissue would occur. If the patient were to twitch during insertion of the electrode through the temporary device, reduced/no relative movement of the device/needle relative to the brain would occur, and so again, reduced/no damage to brain tissue would occur.

Figure 21:
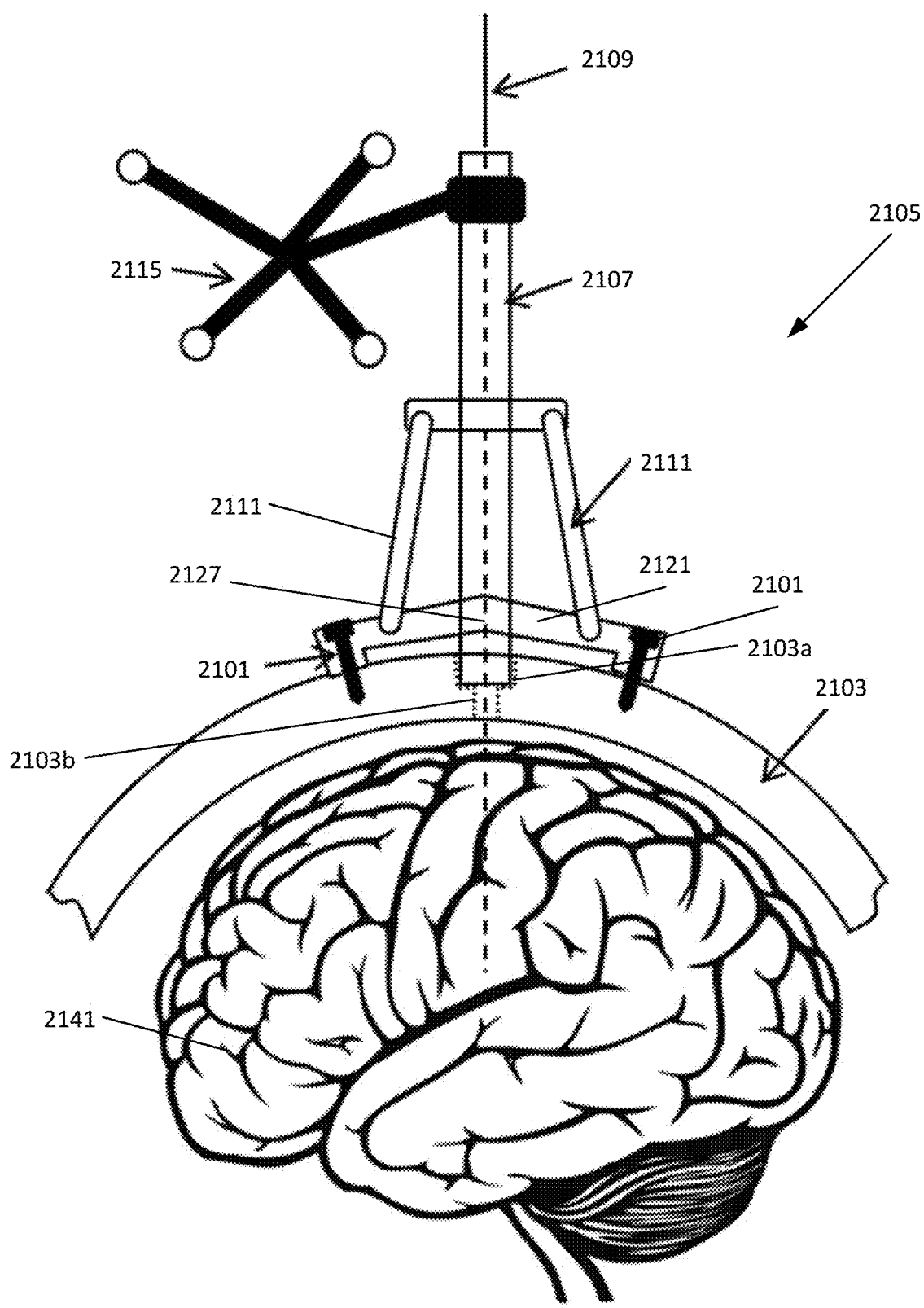
FIG. 21 is a diagram illustrating a temporary cranial insertion fixture according to some embodiments of inventive concepts.

Such a temporary guide fixture may need to be delivered to its attachment point on the skull and attached without the process of attachment causing substantial shift in its position. The temporary guide fixture should be stable in its interface with the skull during the time of its usage. A design for such a temporary guide fixture 2105 is shown in FIG. 21 according to some embodiments of inventive concepts. In some embodiments, the temporary guide fixture 2105 may allow some adjustability after it has been mounted to the skull 2103, and after a tracking element 2115 (also referred to as a tracking array) has been attached to it.

FIG. 21 shows the skull 2103 with a temporary cranial insertion fixture 2105 (also referred to as a temporary guide fixture, temporary needle guide/structure, or temporary electrode guide/structure) attached to the skull 2103 with screw anchors 2101 and including a guide tube 2107. The distal end of guide tube 2107 (adjacent base 2121 of the fixture) rests in a recess 2103a in the skull 2103 for stability. A central hole through guide tube 2107 is used to guide insertion of a medical device 2109 (such as a needle or electrode). The guide tube 2107 may have some angular adjustability through 2 or more telescoping adjustment members 2111 and/or a moveable coupling 2127 to compensate for alterations in a desired trajectory after attachment or shift in tube position occurring during the attachment process. According to some embodiments, guide tube 2107 may be coupled with base 2121 of the cranial insertion fixture 2105 using a moveable coupling 2127 such as a spherical joint to allow angular movement of guide tube 2107 relative to base 2121. A tracking array 2115 may allow tracking of the tube position and trajectory once it is mounted to the skull 2103, providing additional feedback on the final position of the temporary needle guide tube 2107. Tracking arrays are discussed above, for example, with respect to tracking array 612.

Figure 22:
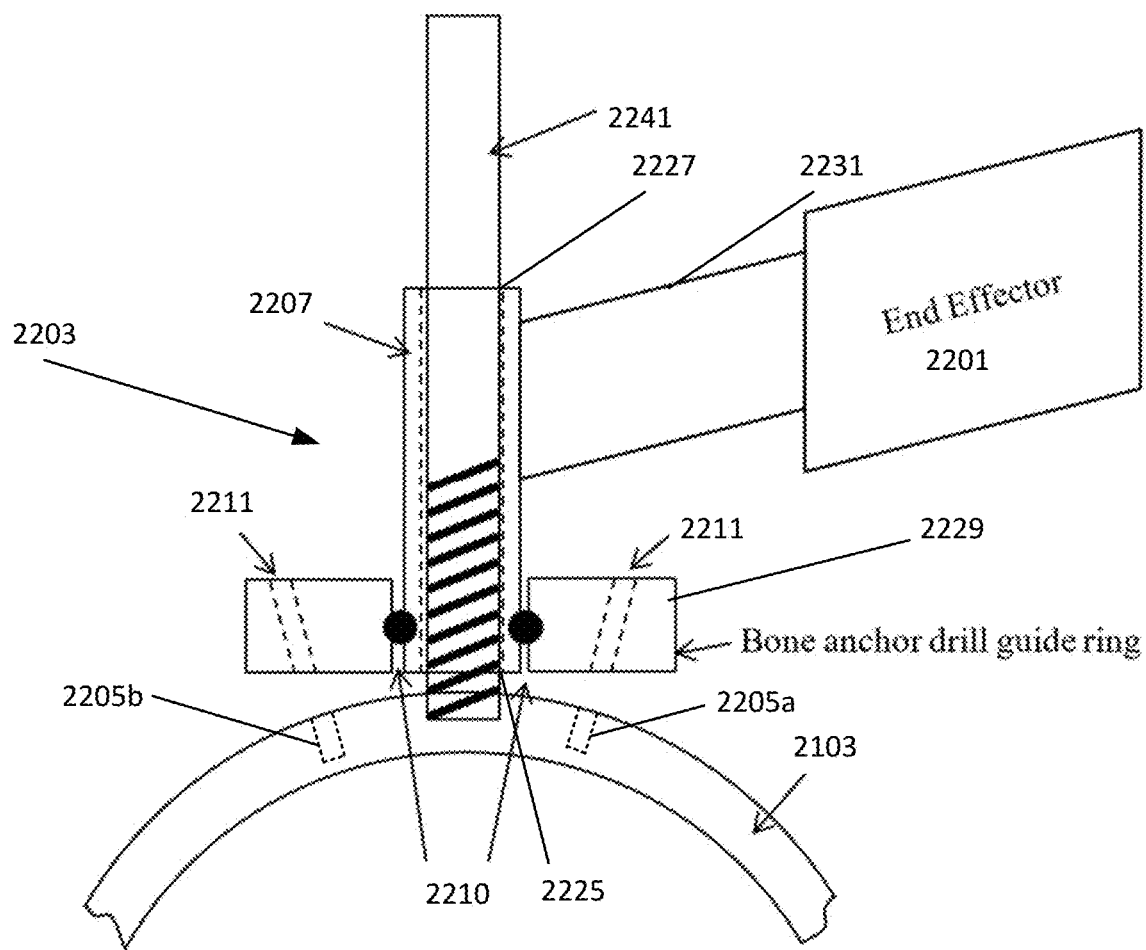
FIG. 22 is a diagram illustrating a drill guide fixture according to some embodiments of inventive concepts.

A process to prepare the skull 2103 to receive the cranial insertion fixture 2105 (also referred to as a temporary needle guide fixture) of FIG. 21 may include the robotic guidance system registering, planning, and auto-positioning the robotic end effector 2201 of FIG. 22 at a position adjacent to the skull 2103 where the robot's end effector 2201 can position drill guide fixture 2203 as shown in FIG. 22. This drill guide fixture 2203 may allow guided drilling of the central hole (shown as recess 2103a of FIG. 21) and pilot holes 2205a-b used to hold anchor screws 2103a-b of FIG. 21 for the cranial insertion fixture 2105 of FIG. 21. The central drill guide 2207 may allow the central burr hole (shown as recess 2013a of FIG. 21) to be drilled partially through or fully through the skull 2103. A partial instead of complete burr hole may allow delivery of cranial insertion fixture 2105 to the skull 2103 and secure attachment of cranial insertion fixture 2105, after which a second drill with a smaller bit could be guided by the guide tube 2107 of cranial insertion fixture 2105 (instead of the robot) to create a burr hole 2103b all the way through the skull 2103. Since cranial insertion fixture 2105 (which may also serve as a drill guide for this smaller diameter secondary through-hole 2103b) is navigated, the secondary drill may operate in conjunction with an adjustable drill stop to provide that the secondary drill penetrates exactly to the thickness of the skull 2103 without over-penetration (which could damage the brain).

Drill guide fixture 2203 may thus be configured to prepare skull 2103 for attachment of cranial insertion fixture 2105. As shown in FIG. 22, drill guide fixture 2203 may include central drill guide 2207 defining a central drill guide hole therethrough, with the central drill guide hole having a first opening 2225 at a base of the drill guide fixture and a second opening 2227 spaced apart from the base of the drill guide fixture. As further shown in FIG. 22, drill guide fixture 2203 may include a bone anchor drill guide 2229 at the base of drill guide fixture 2203, with the bone anchor drill guide 2229 defining a plurality of (e.g., at least three) bone anchor drill guide holes 2211 therethrough spaced around the bone anchor drill guide 2229. According to some embodiments, the bone anchor drill guide 2229 may be provided as a ring (or other geometry/shape) surrounding central drill guide 2207, and each bone anchor drill guide hole 2211 may be offset from the central drill guide hole in a direction that is perpendicular with respect to a direction of the central drill guide hole. In the orientation of FIG. 22, the central drill guide hole is oriented in a vertical direction, and each of the bone anchor drill guide holes is horizontally offset relative to the central drill guide hole. Moreover, each bone anchor drill guide hole 2211 may correspond to a respective hole in base 2121 of cranial insertion fixture 2105 for screws 2101, so that holes in base 2121 of cranial insertion fixture 2105 match with respective pilot holes 2205 drilled using bone anchor drill guide holes 2211.

As further shown in FIG. 22, rotational coupling 2210 (e.g., a rotational bearing) may be provided between central drill guide 2207 and bone anchor drill guide 2229 so that bone anchor drill guide 2229 is rotatable relative to the central drill guide. The central drill guide hole and each of the bone anchor drill guide holes may be cylindrical. Moreover, an axis of rotation of bone anchor drill guide 2229 may be parallel (e.g., coincident) with respect to an axial direction of the central drill guide hole. In addition, a first opening of each bone anchor drill guide hole 2211 adjacent the base of drill guide fixture 2207 may be closer to the central drill guide hole than a second opening of the respective bone anchor drill guide hole spaced apart from the base of the drill guide fixture. Accordingly, each bone anchor drill guide hole 2211 may be non-parallel with respect to central drill guide hole 2227.

As further shown in FIG. 22, a width (e.g., diameter) of the central drill guide hole may be greater than widths (e.g., diameters) of bone anchor drill guide holes 2211. According to some embodiments, central drill guide hole and bone anchor drill guide holes may be cylindrical. In addition, a connector 2231 may be configured to provide a detachable coupling with an end effector 2201 of a robotic actuator.

Figure 20:
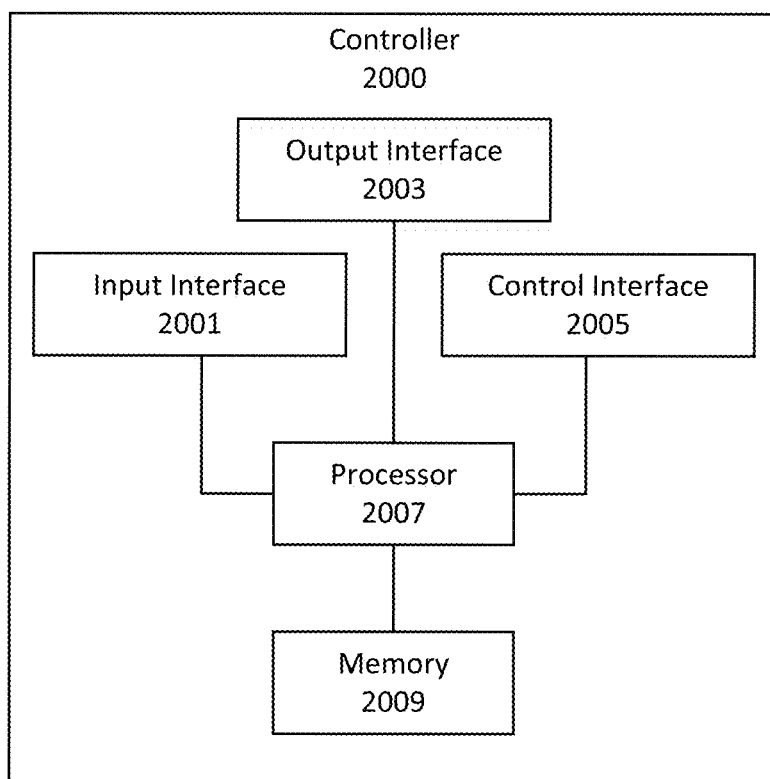
FIG. 20 is a block diagram illustrating a robotic controller according to some embodiments of inventive concepts.

FIG. 20 is a block diagram illustrating elements of a controller 2000 (e.g., implemented within computer 408 and/or computer subsystem) for a robotic surgical system. As shown, controller 2000 may include processor circuit 2007 (also referred to as a processor) coupled with input interface circuit 2001 (also referred to as an input interface), output interface circuit 2003 (also referred to as an output interface), control interface circuit 2005 (also referred to as a control interface), and memory circuit 2009 (also referred to as a memory). The memory circuit 2009 may include computer readable program code that when executed by the processor circuit 2007 causes the surgical robotic system to perform operations according to embodiments disclosed herein. According to other embodiments, processor circuit 2007 may be defined to include memory so that a separate memory circuit is not required.

As discussed herein, operations of a surgical robotic system may be performed by controller 2000 (including processor 2007, input interface 2001, output interface 2003, and/or control interface 2005). For example, processor 2007 may receive user input through input interface 2001, and such user input may include user input received through foot pedal 544, tablet 546, etc. Processor 2007 may also receive position sensor input from tracking system 532 and/or cameras 200 through input interface 2001. Processor 2007 may provide output through output interface 2003, and such output may include information to render graphic/visual information on display 304 and/or audio output to be provided through speaker 536. Processor 2007 may provide robotic control information through control interface 2005 to motion control subsystem 506, and the robotic control information may be used to control operation of a robotic actuator such as robot arm 104 (also referred to as a robotic arm) and/or end-effector 112 (shown as end effector 2201 in FIG. 22). Processor 2007 may also receive feedback information through control interface 2005. Operations of a surgical robotic system (including a robotic actuator configured to position a surgical end-effector and/or a drill guide fixture 2203 with respect to an anatomical location of a patient (such as skull 2103) will be discussed below according to some embodiments of inventive concepts. For example, modules may be stored in memory 2009 of FIG. 20, and these modules may provide instructions so that when the instructions of a module are executed by processor 2007, processor 2007 controls the robotic actuator and/or end effector to perform respective operations.

According to some embodiments of FIG. 22, a surgical robotic system may include the drill guide fixture 2203 coupled with the robotic actuator, such as a robotic arm 104 through end effector 2201. As discussed above, drill guide fixture 2203 may be configured to prepare a skull for attachment of a cranial insertion fixture 2105 (shown in FIG. 21) that is used to insert a medical device (such as a needle and/or electrode) through the skull and into a brain. Elements of drill guide fixture 2203 are discussed above with respect to FIG. 22. The robotic actuator (e.g., robotic arm 104) may be defined to include end effector 2201, and drill guide fixture 2203 may be detachably coupled with the robotic actuator and/or end effector 2201. Moreover, the robotic actuator may be configured to position drill guide fixture 2203. Controller 2000 (e.g., including processor 2007, memory 2009, control interface 2005, etc.) may be coupled with the robotic actuator as discussed above (e.g., through control interface 2005), and controller 2003 may be configured to control the robotic actuator to move drill guide fixture 2003 to skull 2103 based on medical imaging information related to the skull and/or the brain and based on a planned trajectory for insertion of the medical device into the brain.

With drill guide fixture 2203 robotically positioned as discussed above based on a planned trajectory for the medical device (e.g., a needle or an electrode), the doctor can insert an appropriate drill and/or drill bit 2241 through the central drill guide 2207 to drill the central hole in skull 2103 as shown in FIG. 22. The doctor can insert an appropriate drill and/or drill bit (e.g., smaller than drill bit 2241) through bone anchor drill guide holes 2211 to drill the pilot holes 2205 to be used for bone anchor screws 2101. By providing a rotational coupling 2210 between bone anchor drill guide 2229 and central drill guide 2207, the doctor may rotate the bone anchor drill guide 2229 to orient the anchor drill guide holes 2211 (and resulting pilot holes 2205) in a desired location on the skull. Once the doctor has rotated the bone anchor drill guide 2229 to a desired orientation, a locking mechanism may be used to lock the orientation of the bone anchor drill guide 2229 relative to the central drill guide 2207 so that the bone anchor drill guide 2229 does not move while using bone anchor drill guide holes 2211 to drill pilot holes 2205 into skull 2103. Bone anchor drill guide holes 2211 are thus arranged to provide pilot holes 2205 in skull 2103 that match holes in base 2121 of fixture 2105 for screws 2101. Accordingly, rotation of bone anchor drill guide 2229 may be locked before drilling pilot holes 2205 to maintain an appropriate orientation of pilot holes 2205 relative to each other.

Once the robotically placed drill guide fixture 2203 has been used to drill the central and pilot holes as discussed above, the robotic actuator, end effector, and drill guide fixture can be moved away from the skull to allow attachment of cranial insertion fixture 2105 using the central and pilot holes. As shown in FIG. 21, screws 2101 may be provided through base 2121 and into pilot holes 2205 to secure cranial insertion fixture 2105 to skull 2103, and a base of guide tube 2107 may be seated in recess 2103a (formed using drill 2241 and central guide tube 2207). According to some embodiments, adhesive pads may be used instead of screws 2101 to secure base 2121 to skull 2103. According to some other embodiments, guide tube 2107 may be anchored to skull 2103 at recess 2103a so that screws 2101 are not needed to secure base 2121 to skull 2103. In such embodiments, screws 2101 may be omitted, or screws 2101 may be provided to push against the skull (without penetrating the skull) to adjust an orientation of guide tube 2107 (e.g., providing different spacings between different locations of base 2121 and skull 2103).

After delivering cranial insertion fixture 2105 and attaching it to the skull 2103, the needle guide tube 2107 may require further trajectory adjustment due to some shift in tube position during the insertion process or due to the surgeon changing the desired trajectory. The exact position of the mounted temporary needle guide device may be known because it has an attached tracking array 2115 and this array is tracked relative to a previously attached and registered DRB. An adjustment mechanism may be provided that is part of the temporary needle guide fixture 2105 of FIG. 21. It may only be necessary for such an adjustment mechanism to allow small adjustments. If large adjustments are needed, a different through hole and anchor pilot holes may be drilled, and the entire needle guide device may be repositioned. In embodiments of FIG. 21, the adjustment mechanism may include telescoping adjustment members allowing only angulation of the tube. The adjustment mechanism may also enable linear shifts in the position of the tube. The adjustment mechanism may thus include one or more different telescoping, angulating, or otherwise adjustable members/mechanisms 2111 that the user can independently adjust according to instruction from the software and/or while watching feedback from the optical tracking. The adjustable members/mechanisms 2111, for example, may be electrically and/or hydraulically actuated members operating under the control of controller 2000 based on optical feedback from cameras 200 using tracking array 2115, medical image information (e.g., a CT scan or MIll) for skull 2103 and brain 2141, and/or a planned trajectory for the medical device.

Cranial insertion fixture 2105 may thus be configured to provide guidance to insert a medical device (e.g., a needle and/or an electrode) into brain 2141. As shown, cranial insertion fixture 2105 may include base 2121, guide tube 2107, moveable coupling 2127, and adjustment member(s) 2111. Base 2121 may include a plurality of spaced apart contact areas configured to provide contact with skull 2103 and a plurality of spaced apart anchor screw holes for screws 2101. The screw holes, for example, may be provided at respective contact areas.

Guide tube 2107 may be coupled with base 2121, with guide tube 2107 including a contact end and an insertion end. Moreover, the contact end may be configured to contact an opening 2103a in skull 2103, and the insertion end (spaced apart from skull 2103) may be configured to receive medical device 2109. In addition, moveable coupling 2127 may be provided between base 2121 and a first portion of guide tube 2107, and adjustment member(s) 2111 may be coupled between base 2121 and a second portion of guide tube 2107. Moreover, moveable coupling 2127 may be a spherical joint configured to allow angular movement of the guide tube 2107 relative to base 2121.

According to some embodiments, three adjustment members 2111 may be provided, and each adjustment member may include at least three telescoping adjustment members coupled between base 2121 and the second portion of guide tube 2107. Moreover, the telescoping adjustment members may be configured to lock the guide tube in different angular orientations relative to the base. Each adjustment member may comprise a telescoping actuator (e.g., a manually, electrically, and/or hydraulically actuated actuator) configured to move guide tube 2017 to different angular orientations relative to base 2121. According to some embodiments, such actuators may be controlled by controller 2000 to automatically set a trajectory of guide tube 2017 based on medical imaging information, positioning information determined using tracking array 2115 coupled with guide tube 2107, and/or a planned trajectory.

FIG. 22 shows robotic positioning of a drill guide 2203 to prepare the skull 2103 to receive cranial insertion fixture 2105. The central drill guide 2207 guides drilling of the main hole (shown as recess 2103a in FIG. 21) through which the needle is to be inserted. The purpose of the bone anchor drill guide holes 2211 is to guide drilling of the pilot holes 2205a and 2205b for the bone anchor screws 2101 that hold cranial insertion fixture 2105 attached to the skull 2103. In this embodiment, the bone anchor drill guide 2229 may include three or more bone anchor drill guide holes 2211, and bone anchor drill guide 2229 may be connected to central drill guide 2207 by a rotational bearing 2210 so that the holes 2205 can be rotationally positioned where desired in/on skull 2103 relative to the central hole 2103a.

According to some embodiments discussed with respect to FIGS. 23-26, cranial electrode and/or needle insertion can be performed without requiring a pin-based skull frame to be attached, thereby reducing the morbidity of the procedure. Moreover, cranial electrode and/or needle insertion may be performed using robotic assistance instead of requiring an attached arc mechanism, increasing the speed and/or accuracy of the procedure.

Positioning of implants may currently use a relatively large burr hole through the cranium/skull, often over 14 millimeters in diameter. By using a hole of this size, the surgery may no longer be considered minimally invasive surgery (MIS). Additionally, the large size of the hole may provide an avenue for leakage of Cerebrospinal Fluid (CSF). Leakage of this fluid may cause a change in pressure in the skull and/or a shift of the brain within the skull. Such hole sizes may also require a cosmetically undesirable implant to cover the hole after electrode placement.

Embodiments of inventive concepts may combine methods of implant guidance and locking mechanisms to accurately guide an electrode implant to a target location in the brain while simultaneously plugging the hole in order to reduce/prevent leaks, all while using a small enough incision to be considered MIS. According to such embodiments, the surgeon may insert a medical device (e.g., electrode) through a smaller hole, and secure the hole with better cosmesis while also plugging the hole to reduce pressure change and brain shift. According to some other embodiments, an electrode may be inserted after a robotic positioner has been removed.

In current methods of brain electrode placement, the electrode and its retaining implant may be inserted through a large burr hole in the skull. The large burr hole (often 14 mm or more in diameter) may be useful to allow the electrode position to be adjusted during surgery. However, once the electrode is in place, a permanent cover may need to be implanted to hold the electrode in its final location relative to the skull, clamping the wire to prevent it from moving, while allowing the extracranial portion of the wire to be routed subcutaneously. As discussed above, such implants may be cosmetically undesirable.

Current implant retention designs may thus be bulky and may thus require a large patch of hair to be shaved for the procedure. Moreover, the implant cover may leave a bump under the scalp after healing if careful milling is not performed.

According to some embodiments of inventive concepts, it may be possible to insert electrodes through a smaller hole (than has been used for conventional procedures) due to the high accuracy of a surgical robot and more flexible positioning range. The smaller hole may leave a smaller gap between the electrode and the edge of the burr hole, which may allow the electrode attachment device to be smaller. In some embodiments, the implant may also effectively seal the skull and reduce/prevent changes in pressure and/or CSF leaks.

Figure 23:
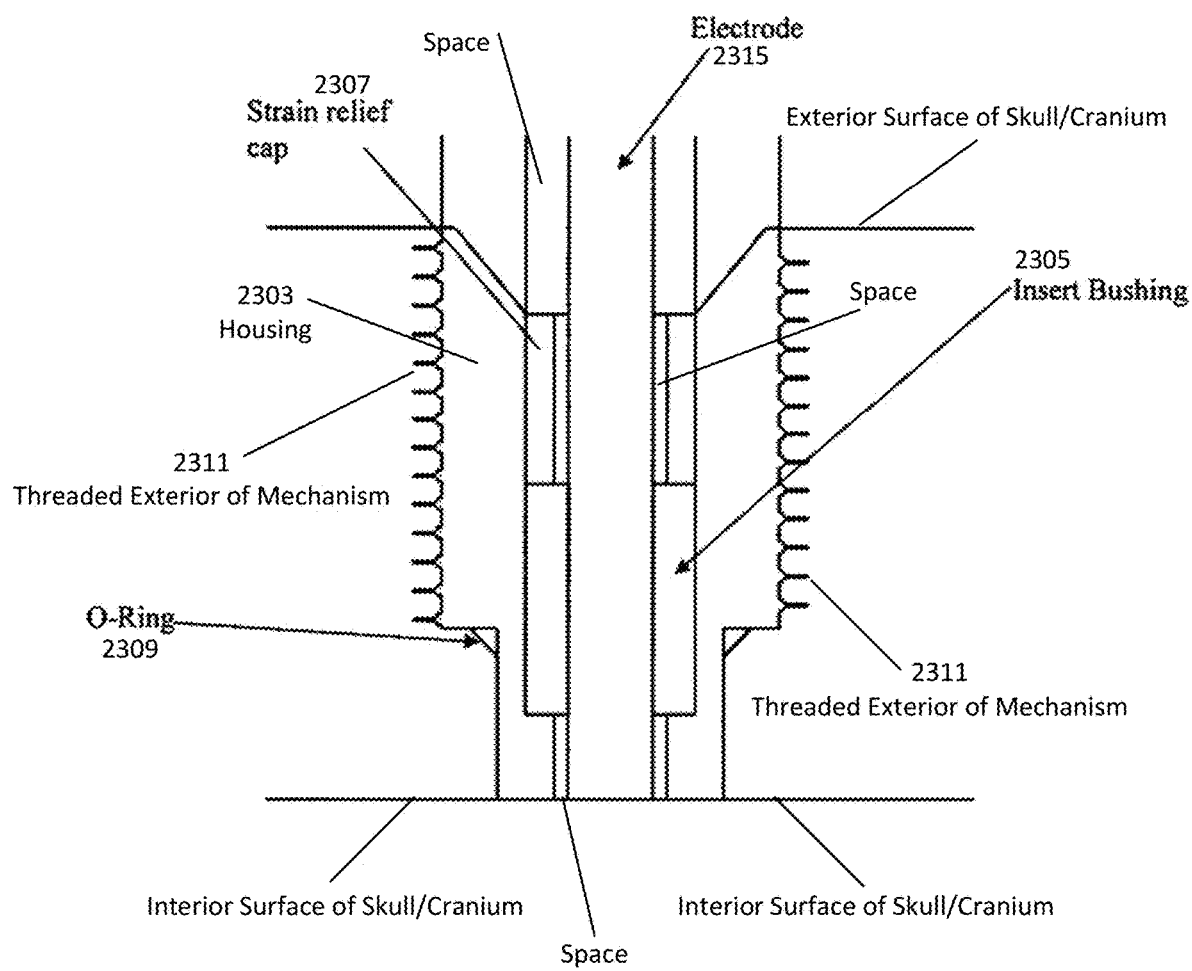
FIG. 23 is a cross sectional view illustrating an electrode retention implant according to some embodiments of inventive concepts.

FIG. 23 is a cross sectional view illustrating an electrode retention implant according to some embodiments of inventive concepts. As shown, the electrode retention implant may be placed in a hole through the skull (also referred to as the cranium). The threaded exterior 2311 of the mechanism allows for grip once in the skull and stability once fully installed. As shown, the guidance mechanism may include housing 2303, compressible insert bushing 2305, strain relief cap 2307, and o-ring 2309. The guidance mechanism of FIG. 23 may thus be used to guide insertion of a medical device (such as electrode 2315 or a needle) into the brain. After planning a desired electrode trajectory on the patient's medical image volumes (MRI and/or CT image volumes), the robotic system may automatically move into place and hold a guide tube in the planned trajectory, positioned just above the skull, similar to methods used with robotic screw placement in the spine. Through the robotically positioned guide tube (not shown), the surgeon may drill a hole through the skull. Then, the surgeon may insert the electrode retention implant into the hole in the skull.

In some embodiments, the burr hole in the skull may be tapped to leave threads that can engage corresponding threads of the electrode retention implant. In some other embodiments, the bone may be left untapped, and the threads of the electrode retention implant may be self-cutting. In still other embodiments, the burr hole may be left untapped, and the electrode retention implant may be fastened in the skull using peripheral set screws, or by gluing, crimping, and/or clamping into the skull.

When the electrode retention implant is fastened to the skull, a primary fluid pathway may be through its center hole (through which the electrode will pass). Although a secondary fluid pathway may be possible along an outer edge of the implant where it interfaces with the skull, o-ring 2309 (e.g., comprising a biocompatible and possibly resorbable elastomeric material) may help to seal this outer portion to reduce/prevent fluid leakage. In other embodiments, a layer of gel and/or paste may be used instead of or in addition to the o-ring to help seal an outer portion of the skull-implant interface. The center hole may be concentric with respect to the electrode and may house the locking electrode retention mechanism.

FIG. 23 is a cross sectional view illustrating the electrode retention implant placed in a hole in the skull. The threaded exterior 2311 of the implant allows for grip with the skull and stability once fully installed. The O-ring 2309 helps seal the implant-bone interface. The strain relief cap 2307 is a sliding metal piece that compresses the insert bushing 2305 when forced downward. Note that the strain relief cap 2307 has a larger inside diameter than the outside diameter of the electrode so that it does not force the electrode 2315 to advance when moved downward. The insert bushing 2305 may be made of an elastomeric material such that when it is compressed by the strain relief cap 2307, it expands toward the center of the hole (toward electrode 2315) gripping the electrode without causing it to advance.

Figure 24:
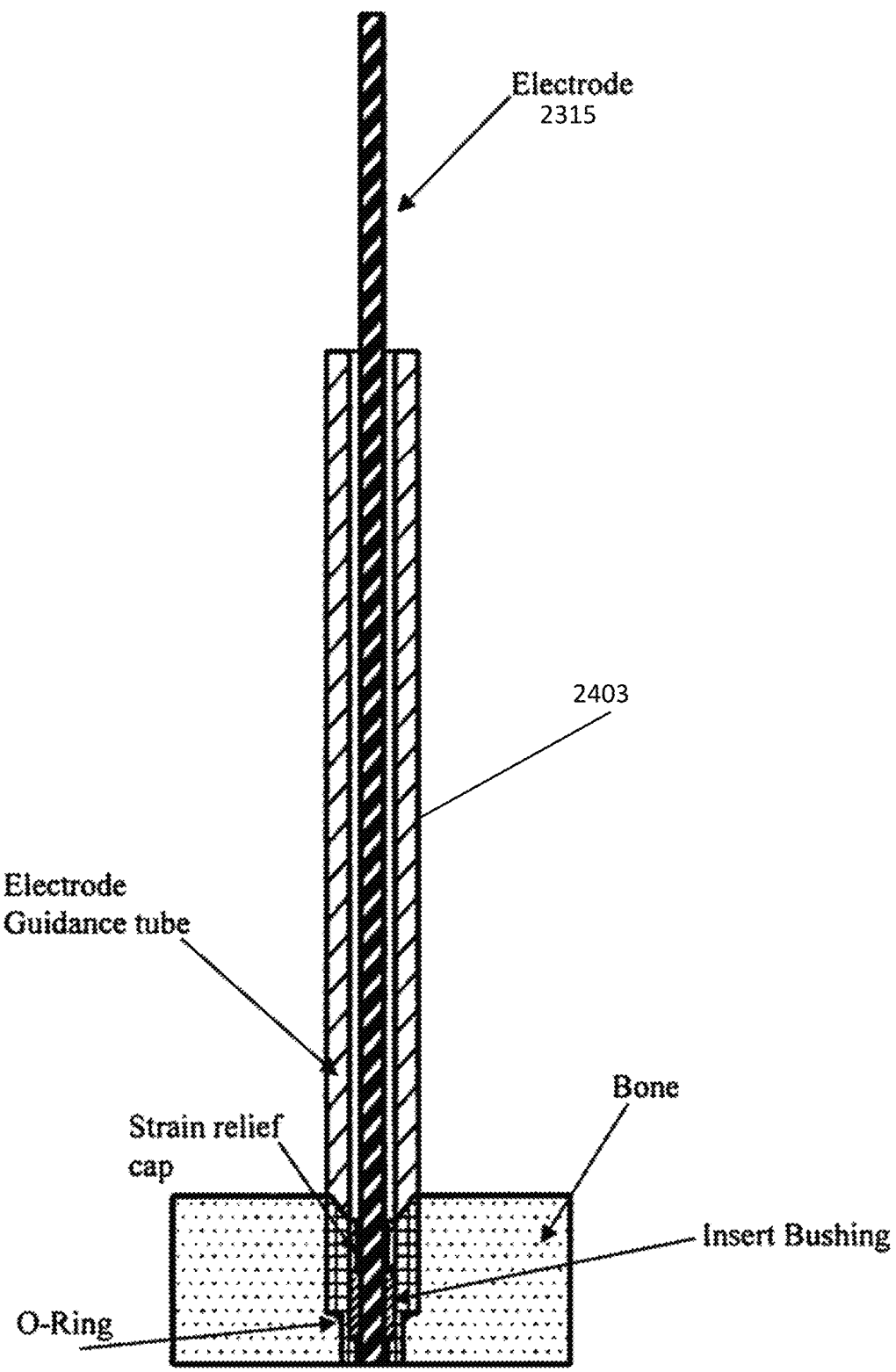
FIG. 24 is a cross sectional view illustrating an electrode guidance tube according to some embodiments of inventive concepts.

The electrode retention implant may be detachably interconnected with an electrode guidance tube 2403 as shown in FIG. 24, and the electrode guidance tube 2403 may be used to insert the electrode retention implant (shown at the bottom of tube 2403 in FIG. 24), for example using the electrode guidance tube 2403 as a screwdriver, and to guide passage of the electrode concentrically along a desired trajectory. Alternatively, two separate tools may be used. For example, a first driver tool may be used to insert the electrode retention implant, and then an electrode guide tube may be connected to the electrode retention implant and used to guide the passage of the electrode along the desired trajectory. In some embodiments, the electrode guidance tube may have threads located bottom of the chamfer that interlock with threads in the chamfered top edges of the electrode retention implant. The electrode itself may then be inserted through the wire guide to its desired depth. Once the electrode is in place, a mechanism may be deployed that forces the strain relief cap downward (toward/into the skull), compressing the bushing that retains the electrode.

In some embodiments, the electrode retention device may also have a set screw mechanism proximal to the strain relief cap 2307 so that when the set screw is advanced, the strain relief cap 2307 is forced downward (toward/into the skull), compressing insert bushing 2305. The set screw may be left in place as part of the implant to keep the insert bushing compressed. In other embodiments, a plunger within the electrode guidance tube may be forced down to force the distal strain relief cap downward (toward/into the skull) and to compress the insert bushing 2305. While held in this configuration, another mechanism may deploy glue, a crimper, and/or an additional set screw to hold the insert bushing in its compressed state.

As shown in FIG. 24, electrode 2315 may be inserted through the electrode guidance tube and electrode retention implant. The electrode guidance tube may rest in and be rigidly connected with the chamfer of the electrode retention implant.

Figure 25:
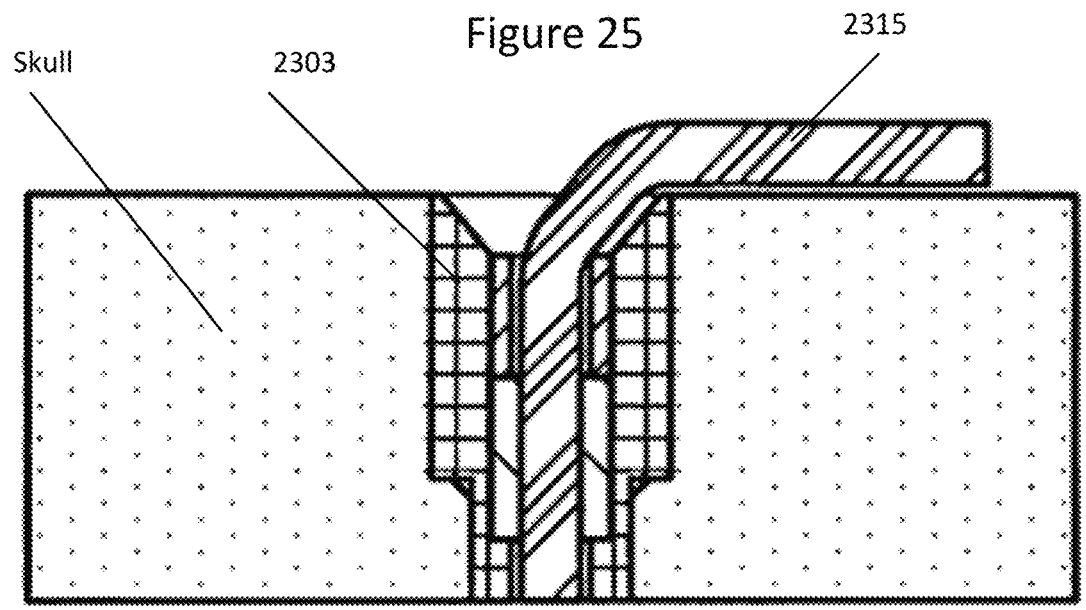
FIG. 25 is a cross sectional view illustrating an electrode retention implant and electrode wires in a skull according to some embodiments of inventive concepts.

After the electrode retention implant and the electrode 2315 are in place and secured, the electrode guidance tube may be removed. The surgeon may then tunnel the implanted electrode 2315 subcutaneously away from the burr hole as shown in FIG. 25. The chamfered edge may provide a gentle transition for the electrode to reduce/prevent damage to the wire when laid flat against the skull as shown in FIG. 25. A pathway for the electrode wire may be that once the electrode retention implant and the electrode are in place, the electrode wire may travel under the skin from the implant location, behind the patient's ear, down the shoulder and into the chest adjacent to the clavicle.

FIG. 25 shows that the electrode wire may pass through the electrode retention implant and curve gradually as it bends 90 degrees to lie flush with the skull after the guide tube has been removed and the gap between the implant and the electrode is sealed. The chamfered or alternately rounded edge may allow a more gradual bend than a plain hole, thereby reducing/preventing wear of the locking mechanism of the implant over time.

According to other embodiments, a cannula may be put in place to guide the electrode to a proper position in the brain. The workflow for such a process may be provided as follows. The surgeon may insert the electrode retention implant then insert the cannula to the desired depth. To make the cannula stiffer and reduce/prevent fluid from entering into it, the cannula may be occupied with a stylet (stiff wire) at the time of insertion. With the cannula and stylet inserted the bushing may be temporarily compressed to hold the cannula. The surgeon may then remove the stylet from the cannula and insert the electrode wire in place of the stylet. Once the electrode is positioned correctly, the surgeon will release compression on the bushing, remove the cannula, and finally re-lock the bushing to the electrode.

In another embodiment of the electrode guidance tube, the temporarily attached tube is used without further robotic assistance to position the electrode to its final depth. An advantage of such a method may be that the robot and stereotactic frame may be out of the way of the surgeon and imaging equipment, and the patient may be taken from the operating room to a different room/facility (such an and imaging suite for MIll and/or CT imaging) that might allow better visualization of structures of the brain relative to the electrode tip and facilitate further adjustment of electrode position with the patient awake or asleep. Such a method may require that the electrode guidance tube remain rigidly in the desired trajectory relative to the skull. The method may therefore require rigid interlocking of the electrode retention implant to the skull and rigid interlocking of the electrode guidance tube to the electrode retention implant as shown in FIG. 24.

Figure 26:
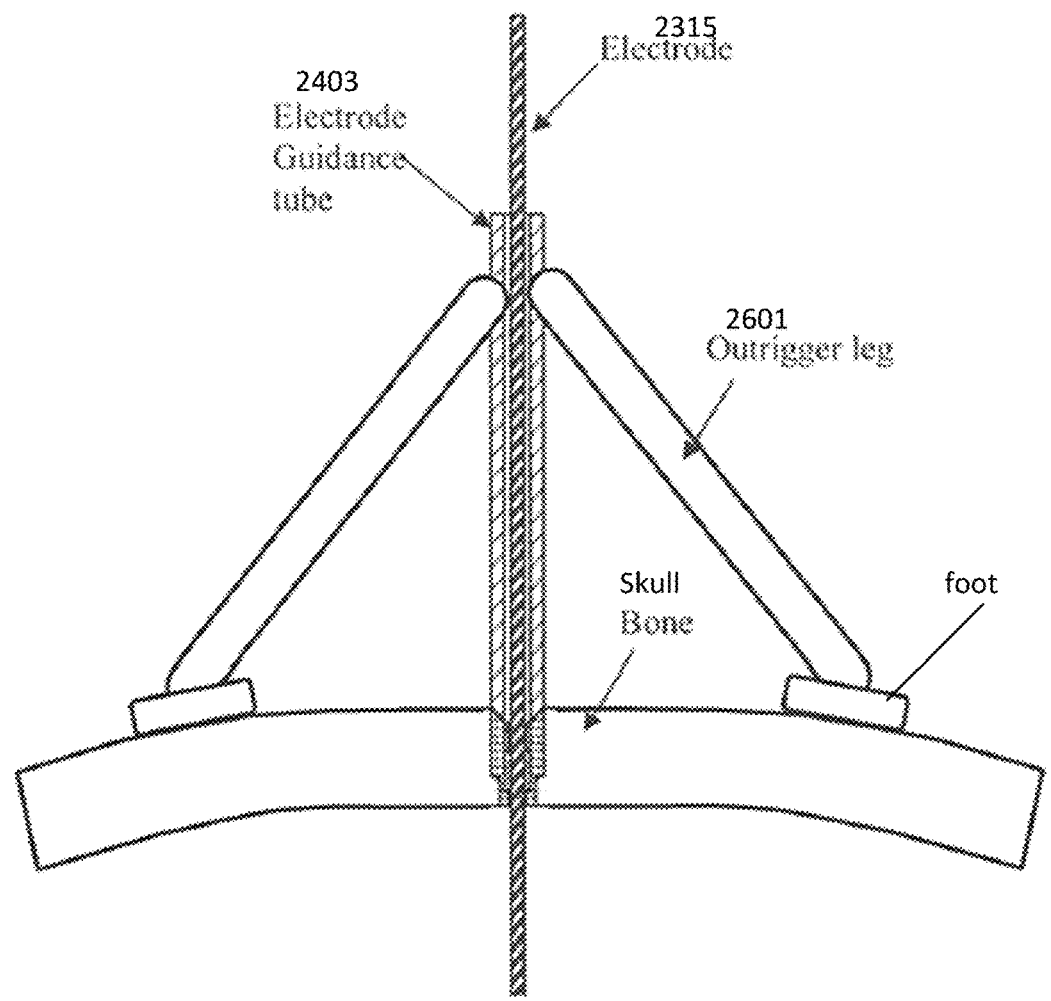
FIG. 26 is a cross sectional view illustrating guide tube support mechanism according to some embodiments of inventive concepts.

Another embodiment may include an additional stabilizing mechanism outside the diameter of the electrode guidance tube as shown in FIG. 26 to further provide that the electrode guidance tube 2315 is maintained in the desired trajectory. Such a stabilizing mechanism may include a plurality of at least three legs 2601 or an extended rim with an adjustment mechanism to allow the stabilizers (e.g., legs) to press against the skull with light force to maintain the static trajectory of the guidance tube.

FIG. 26 illustrates a cutaway side view showing an outrigger mechanism on the electrode guidance tube to maintain the tube's trajectory in a static position relative to the skull after the robotically controlled alignment tube is removed. One or more outrigger legs 2601 may hold the tube in a static position, with three legs providing a desired stability, like a tripod. Legs 2601 may be provided with respective adjustment mechanisms to adjust a pressure of each foot against the skull.

By locking the electrode in place through a small hole, embodiments of inventive concepts may offer a better alternative for brain electrode placement surgery. Such embodiments may reduce CSF leakage due to smaller burr hole size and a more effective/immediate sealing of the hole. The guide may fasten immediately to the skull when inserted rather than requiring additional fasteners to secure. Moreover, final electrode insertion or adjustment may be performed using just the implant and the electrode guide without the robot arm or head frame present, meaning that the patient can be more easily transferred out of the operating room (i.e., to an MRI or other imaging equipment) to finalize electrode placement.

According to some embodiments discussed below with respect to FIGS. 27-31, robotic surgery may be provided without requiring optical and/or electromagnetic tracking of the patient and robot. Such methods may be suited to cranial procedures such as deep brain stimulation DBS electrode placement.

A floor-mounted 5-axis robot may provide (according to the coordinate system of FIG. 27), in order from base to extremity, a vertical linear z-axis followed by rotation about the Z axis at a shoulder joint, followed by a second rotation about the Z axis at an elbow joint connecting upper to lower arm, followed by roll about the lower arm followed by pitch at a wrist joint, with an end effector distal to the wrist joint. Such a robot can be utilized in a mode that does not require optical tracking of the robot or patient. In such a mode, the robot's base coordinate system may be registered directly to the anatomy.

If the robot is well calibrated, it may be possible to determine a position of the end effector based on the positions of each robotic axis (forward kinematics) and to determine the position of each robotic axis used to drive the end effector to a target location and trajectory (inverse kinematics). In the exemplary 5-axis robot mentioned above, if the current dynamic location of each axis is known through, for example, encoders or Hall Effect sensors on the motor of each axis, and if each angular joint rotates in a truly planar fashion, the linear z-axis travels in a truly linear fashion, and manufactured segment lengths and relative joint face angles are accurately known, then forward kinematics can be used to precisely determine the location of the guide tube held by the end effector. Similarly, to drive the robot to where the guide tube on the end effector is in the desired location and orientation, inverse kinematics can be used to calculate the necessary position to send each joint dynamically.

Figure 27:
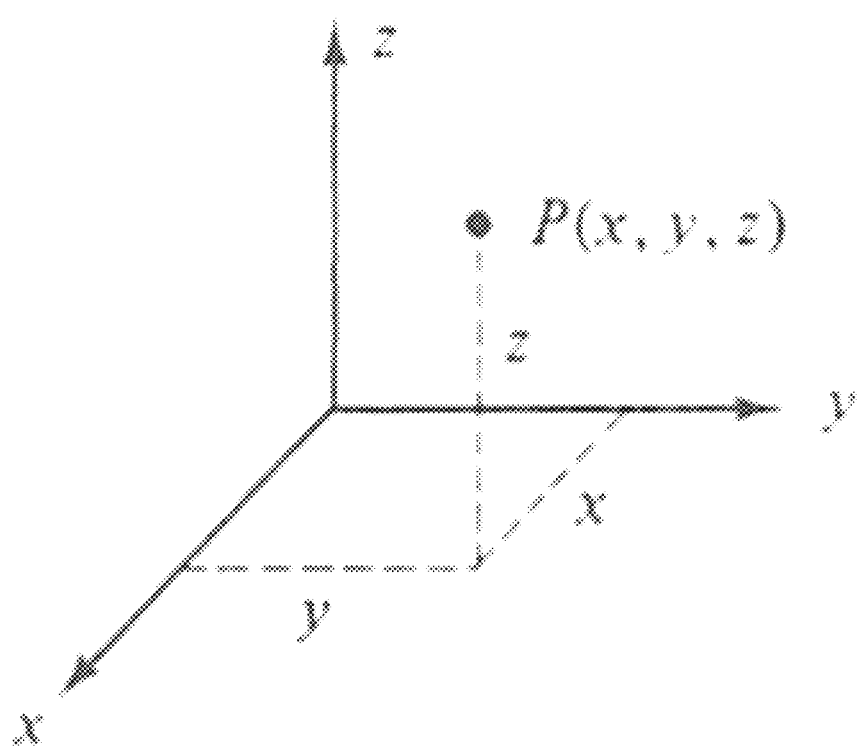
FIG. 27 illustrates a coordinate system for a robotic system according to some embodiments of inventive concepts.

This ability to detect the current end-effector position or drive the position of the end-effector to a desired location can be generalized to an n-axis robot. Desired locations and trajectories in the surgical space may be referenced via a Cartesian coordinate system to the frame on the patient as shown in FIG. 27. Using inverse kinematics, the locations to which each joint should be driven to position the end effector at the desired tip location with the desired trajectory can be determined. Once each joint location is known, the final step is to determine the actuator location that is required to accurately set the joint location. This consideration may be nontrivial given the many different types of actuator designs, which can include linear, rotary, coupled, and non-linear to name a few. For example, a linear actuator could attach to a lever on one side of an angular joint to create an angular movement of the joint, and the required precise actuator position to achieve the desired joint angle should be properly calibrated.

In methods according to some embodiments of inventive concepts, registration may be performed by moving the robot's end effector into position over known landmarks on a patient-mounted reference fixture that is simultaneously rigidly affixed to the patient and the robot base, then automatically sampling the positions of the robot's joints from encoders on each axis and using forward kinematics to determine the locations of the landmarks in the robot's base coordinate system. This procedure may register a head frame relative to the robot coordinate system. Registration of a head frame relative to the anatomical coordinate system is achieved since the reference fixture also contains radio-opaque fiducials in known positions relative to the head frame. These fiducials are detected in the CT scan and their locations automatically determined through image processing. With the robot registered relative to the head frame and anatomy registered relative to the head frame, the robot is registered relative to the anatomy. The head frame to which the reference fixture was attached remains rigidly affixed to the patient and robot base for the remainder of the procedure, and so the robot remains registered to patient anatomy as long as this rigid interconnection persists. The surgical procedure can then be completed robotically as is currently done through existing methods using optical tracking.

In cranial procedures, such a reference fixture may include a localizer, such as the N-shaped localizer currently used with the Leksell frame, with additional registration features, as shown in FIGS. 28A, 28B, 28C, and 28D. This reference fixture of FIG. 28B would temporarily mount to the frame of FIG. 28A that is pinned into the patient's skull in FIGS. 28C and 28D, which would itself attach to the robot base (via the arm of FIGS. 28A, 28C, and 28D) to provide rigidity of the frame relative to the robot.

Figure 29A:
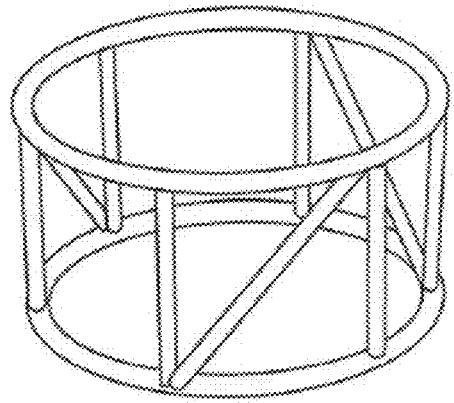
FIGS. 29A, 29B, 29C, and 29D illustrate a head frame used with separate reference fixtures according to some embodiments of inventive concepts.
Figure 29B:
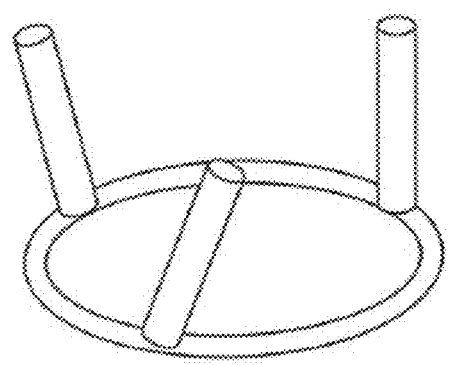
Figure 29C:
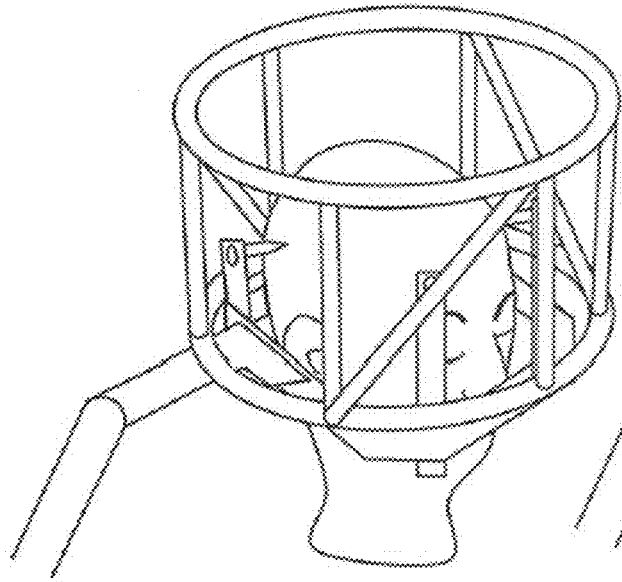
Figure 29D:
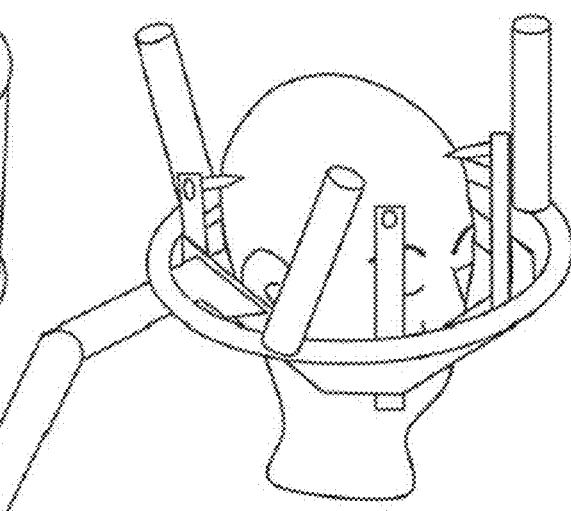

Alternately, the localizer fixture of FIG. 29A and a separate robot reference fixture of FIG. 29B with posts, holes, balls, or sockets may be used sequentially as shown in FIGS. 29C and 29D as long as they anchor to specific locations with a fixed offset relative to the head frame and each other as shown in FIGS. 29A, 29B, 29C, and 29D. For example, the localizer fixture (with N-shaped fiducial rods) of FIG. 29A could connect to the head frame as shown in FIG. 29C before collecting the CT scan. After collecting the CT scan, the localizer fixture could be removed and a robot reference fixture of FIG. 29B with posts could be secured to the frame as shown in FIG. 29D using the same mount points as the localizer fixture. The robot would then be registered by touching the reference points on the robot reference fixture with the robot's end effector. Alternately, the order could be reversed. That is, the registration of robot to head frame could be performed first by moving the robot to touch points on the robot reference fixture, then the robot reference fixture removed, the CT reference fixture attached, and a CT collected. In either case, after performing robot and CT registration, both fixtures would be removed, leaving just the head frame.

Figure 28A:
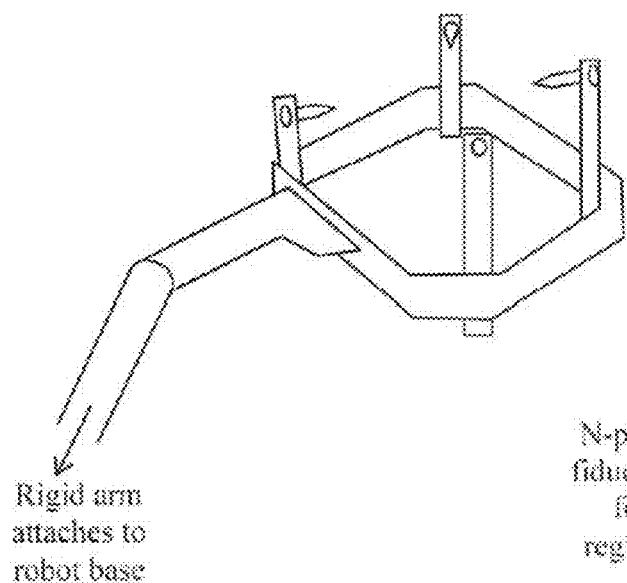
FIGS. 28A, 28B, 28C, and 28D illustrate a head frame and a reference fixture according to some embodiments of inventive concepts.
Figure 28B:
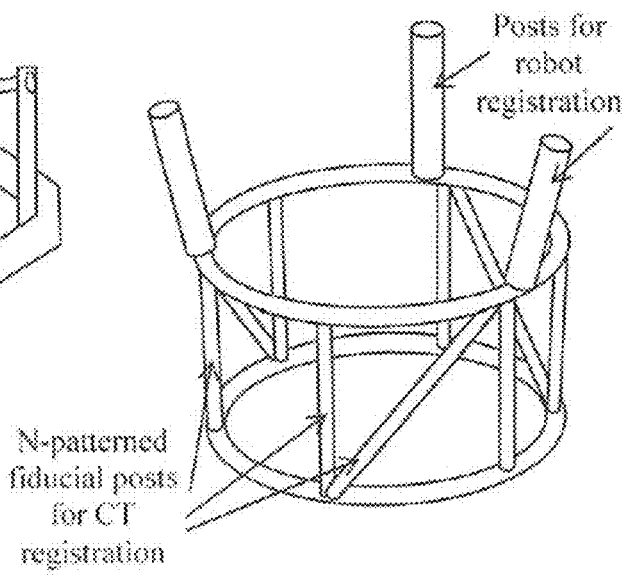
Figure 28C:
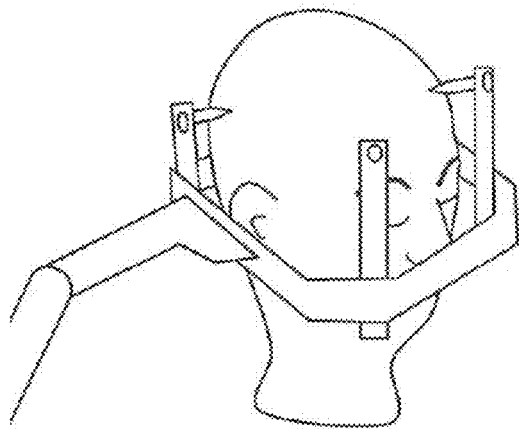
Figure 28D:
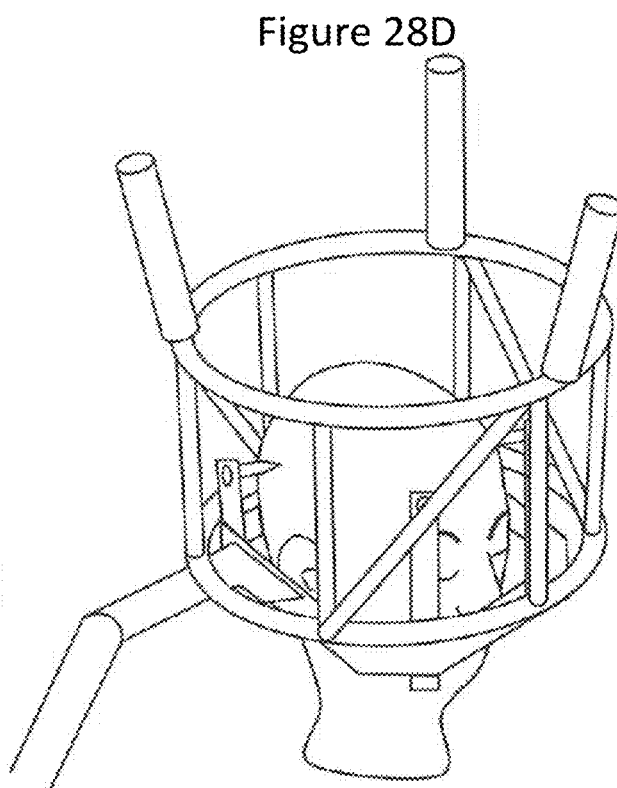

FIGS. 28A-D shows a head frame (e.g., Leksell) and a reference fixture. FIG. 28A illustrates a head frame with a rigid arm that secures it to the robot base. Four threaded pins are visible to secure the head frame to the patient's head. FIG. 28B illustrates a reference fixture with fiducial rods in an N shape to allow CT registration as is currently performed using Leksell frame localizer. In addition, FIG. 28B shows posts that allow robot registration. FIG. 28C shows the frame of FIG. 28A mounted on a patient's head, and FIG. 28D shows the frame of FIG. 28A and the reference fixture of FIG. 28B mounted on the patient's head.

FIGS. 29A, 29B, 29C, and 29D show an alternative sequential method using two separate reference fixtures to perform CT and robot registration. In FIG. 29C, the CT reference fixture (N-shaped localizer) of FIG. 29A attaches to the head frame (e.g., of FIG. 28A) temporarily during the CT scan. In FIG. 29D, the robot reference fixture of FIG. 29B, with posts over which the robot's guide tube passes, attaches temporarily to the head frame for robot registration using the same mount points as the CT reference fixture. In FIG. 29C, the CT reference fixture is attached to head frame and patient, and in FIG. 29D, the robot reference fixture attached to head frame and patient.

Figure 30A:
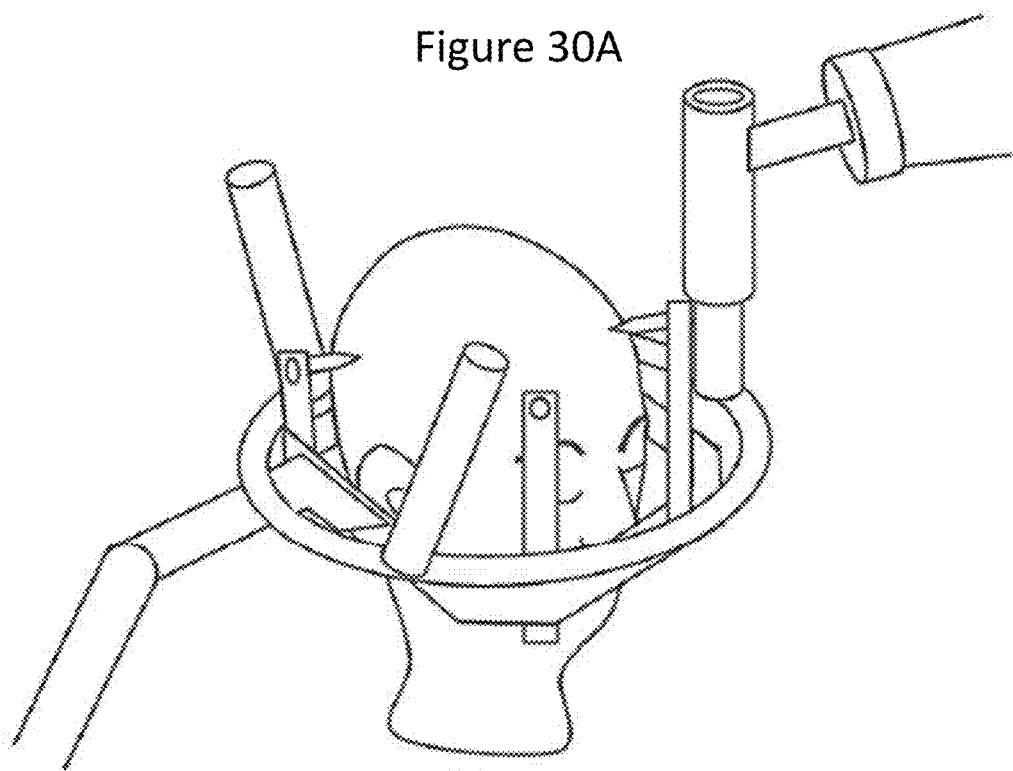
FIGS. 30A and 30B illustrate use of localizing features with a robotic end effector according to some embodiments of inventive concepts.
Figure 30B:
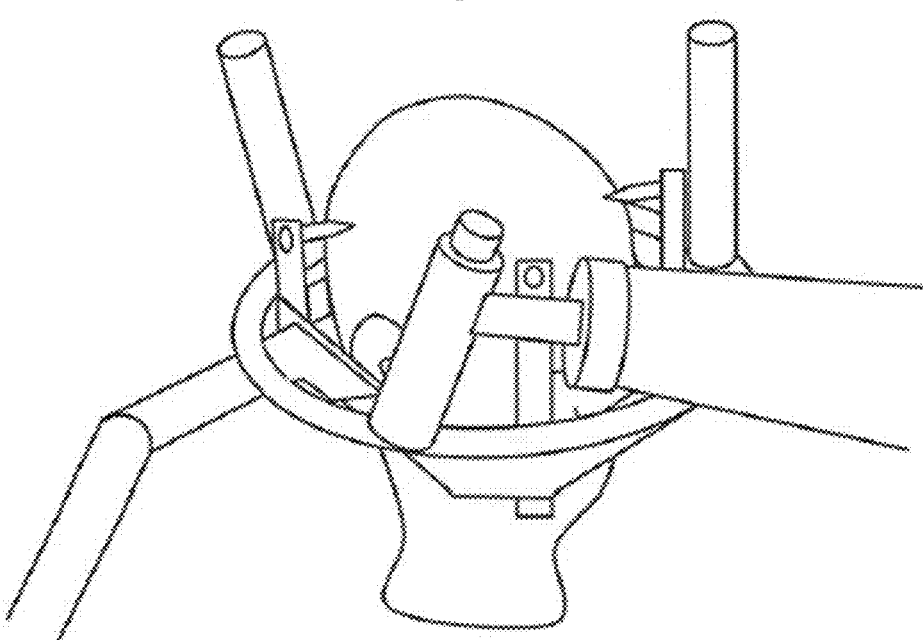

As noted above, for robot registration relative to the head frame, the robot arm may be guided down over posts, holes, balls or sockets on a reference fixture (e.g., of FIG. 28B/D or FIG. 29B/D) that is simultaneously rigidly attached to the patient and robot to establish reference positions. That is, some non-limiting options for mating features on the robot and the robot reference fixture could be: (1) posts on the reference fixture (e.g., as shown in FIGS. 28B/D or 29B/D), over which a tube held by the end effector slides until bottoming out; (2) holes on the reference fixture, into which a post held by the robot's end effector slides until bottoming out; (3) spheres protruding from the reference fixture, over which a socket-shaped assembly held by the robot fits; or (4) sockets on the reference fixture, into which a sphere-ended piece held by the robot fits. Any other suitable mating features could also be effective. Posts or holes may be preferred over balls or sockets because posts/holes may require matching of a line in space and not just a single point, and so it may be more likely that better accuracy will be achieved in the detected position of the features. FIGS. 30A and 30B show the robot being positioned over two of the three posts. For registration, at least two non-parallel posts (lines) may need to be identified or at least 3 points (balls/sockets) may need to be identified. It may also be advantageous to drive the robot all the way down over the post until it bottoms out at a known location along the line, although not necessary to find a solution unless posts are parallel.

The robot can be manually driven over the posts/holes or balls/sockets through joystick control, force control (utilizing a bracelet on the end effector that responds to user-applied forces), or automatic control. Automatic control could include, for example, a force feedback mechanism that guides movement of the robot arm as its guide tube slides over a post on the reference fixture, keeping the post centered within the guide tube. Or automatic control could include optical tracking feedback, where the tracking system detects the posts on the reference fixture and moves the end effector's guide tube down over the posts. Or, automatic control could include a combination of optical and force feedback.

FIGS. 30A and 30B show the robot end effector being manually or automatically guided over localizing features on the reference fixture. In FIG. 30A, the guide tube of the end effector is shown partially over the left rear post, and in FIG. 30B, the guide tube of the end effector is shown fully over (bottomed out on) right front post.

An additional implementation for the step of finding the location of the frame using the robot could be to attach a calibrated camera to the end effector and perform mono-tracking (as opposed to stereo tracking) in visible or infrared IR light. A patterned object may be placed on the head frame in a known position and orientation and the robot could be manually or automatically positioned to register the robot to the head frame. For use with mono-tracking, a pattern that requires viewing from a particular unambiguous vector may be preferred. For example, a "bullseye" with two same- or different-sized rings at different distances where the rings are only concentric at a particular location of the end-effector could be used. Or, a ring pattern applied to a sphere or cone, where the rings are only concentric and circular if the sphere or cone is viewed from a particular orientation could be used. Or a dark pattern could be applied only to a sub-portion of a sphere, such that the camera only views the pattern symmetrically if the end-effector is viewing it from a particular perspective. An example is discussed below with respect to FIG. 31.

Figure 31:
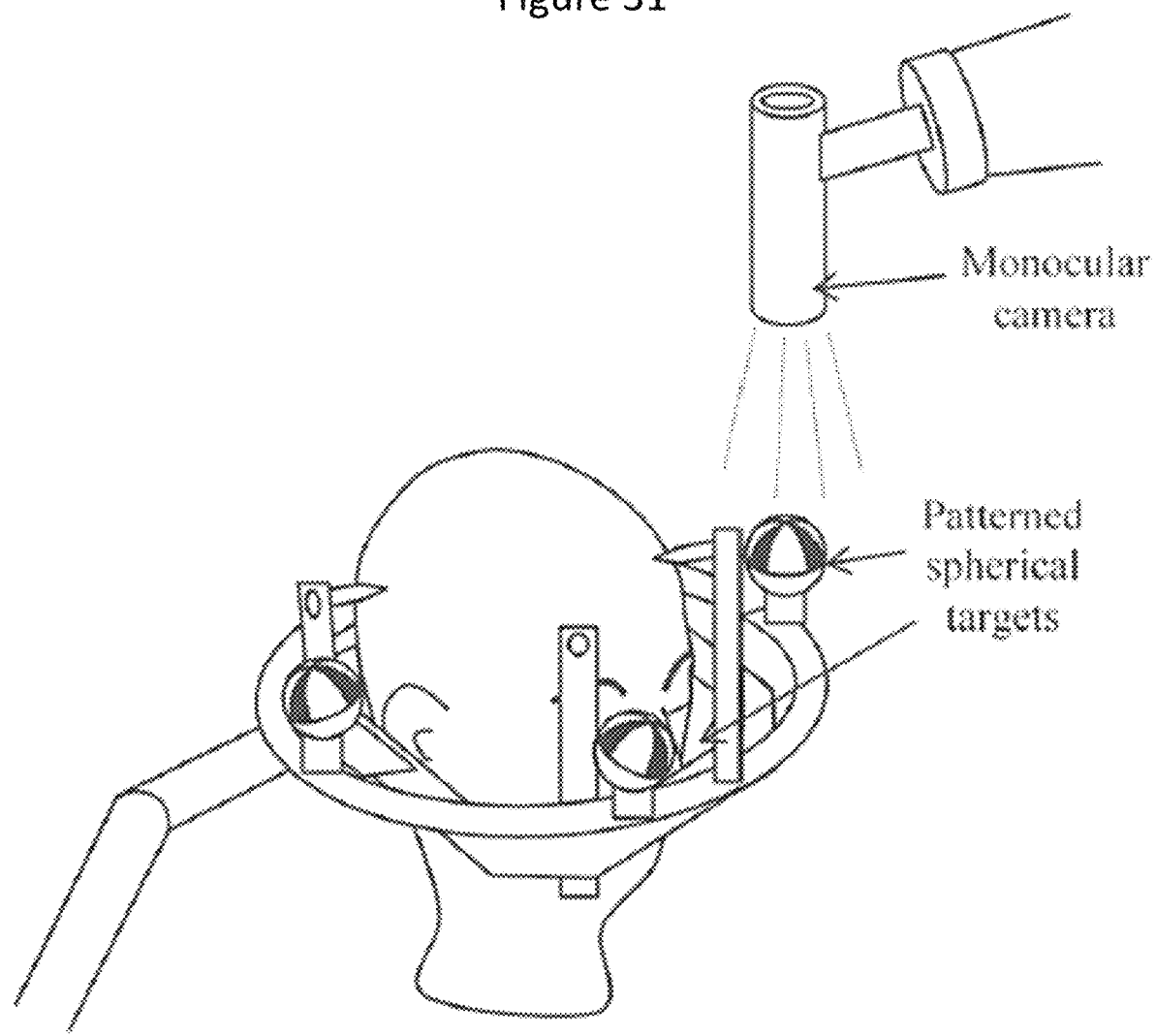
FIG. 31 illustrates use of patterned targets with a robot including a monocular camera according to some embodiments of inventive concepts.

FIG. 31 shows the robot end effector holding a camera that provides a view aligned with the centerline of the tube. The robot is automatically or manually positioned until it is viewing each target from a perspective that renders the target's pattern symmetrical, allowing registration when three or more aligned perspectives are viewed since only one robotic coordinate system can achieve simultaneous alignment of the three perspectives. In this example, the pattern on a hemisphere appears as an 'X', but only when viewed from a straight-on perspective. From other off-axis perspectives, the camera detects the pattern as asymmetrical, with the legs of the X being different lengths and the X off-center.

This method could also be used with conventional binocular optical tracking (e.g., Polaris Spectra, Northern Digital, Inc.) during initial setup. Optical markers could be placed on the head frame, such as the Dynamic Reference Base (DRB), and in or around the guide tube of the end effector, such as the active marker array (AMA) or the Passive Tube Array (PTA). If the DRB location relative to the frame is known and the AMA/PTA location relative to the end effector is known, registration is complete as soon as the cameras capture a frame of tracking information with both DRB and AMA/PTA in view. Since the transformation between DRB and AMA/PTA may be known once tracking data are captured and the robot is rigidly locked to the patient and cannot move, the DRB and AMA/PTA are no longer needed and can be removed or deactivated. With the DRB and AMA/PTA removed/deactivated, robotic inverse and forward kinematics as described earlier would then be used for further positioning during the procedure. If patient repositioning is needed, the robot could be easily re-registered to the new patient position by re-attaching the DRB and re-attaching the PTA or reactivating the AMA and capturing new tracking data.

According to some embodiments of inventive concepts, a robot may be used without requiring optical tracking during the procedure, to reduce/eliminate line-of-sight issues that may be common with current optically tracked robotic systems.

Turning to FIGS. 32A-39B, exemplary embodiments of a detachable drill guide for cranial electrode placement are disclosed. Presently, a method for cranial electrode placement may include a patient tracker or dynamic reference base (DRB) and a method for registering medical images to tracking space. Although it is possible to register and track using a DRB developed for other applications, such as robot assisted spine surgery, and an additional tracked fixture such as an intraoperative CT registration fixture (ICT), the mostly spherical shape of the skull may allow customized registration and tracking fixtures. In the spine, a spinous process clamp or a spike into the ilium is used to mount the DRB. However, in the skull, such a method may be unworkable or infeasible. One way to attach a DRB to the skull such that it cannot rotate or become dislodged is to use multiple screws. However, accordingly to exemplary embodiments of the present disclosure, to keep the number of holes created in a patient's skull to a minimum, a DRB 3200 having a single screw is illustrated in FIGS. 32A-32B. DRB 3200 also has spikes 3202 to add additional frictional stability on the scalp or exposed skull bone without the morbidity of additional holes into the bone.

FIGS. 32A-B show top and bottom views of a cranial DRB 3200. A single screw through an opening 3204 secures DRB 3200 to the skull. Three spikes 3202 on the underside of the DRB provide additional stabilization. DRB 3200 may also include notches 3208 for aligning a registration skirt as described below.

To register, a skirt fixture 3300 of known dimensions with radio-opaque metal spheres 3302 embedded in the skirt frame at known locations relative to optical spheres 3210 of DRB 3200 is temporarily attached (FIG. 33A-B). Fixture 3300 is in place during a CT scan and is then removed after the scan is obtained.

FIGS. 33A-B show DRB 3200 with and without fixture 3300 attached, which is present only during the scan. The fixture locks into the base of DRB 3200 in one orientation, dictated by the asymmetrical notches 3208 visible at the base of DRB 3200. Fixture 3300 may be embedded with multiple bearing balls (BBs), for example seven (7) BBs may be embedded in an asymmetrical pattern that is detected automatically from the CT scan volume using image processing. One or more tracking cameras may track a position of optical tracking spheres 3210 on DRB 3200 and since the positions of tracking spheres 3210 relative to the BBs are fixed and known, registration of tracking to anatomy may be achieved.

Before usage of an electrode placement tool, DRB 3200 would first be attached to the patient's skull in a position away from the electrode site and registered by collecting a CT scan or another type of scan, such as an O-Arm (cone beam CT) scan.

An exemplary electrode guide 3400 consistent with the principles of the present disclosure is illustrated in FIGS. 34A-C. FIGS. 34A-C illustrate guide tube 3402 and accessories. FIG. 34A illustrates guide tube 3402 with a detachable electrode holder 3404 at a distal tip of guide tube 3402. Electrode holder 3404 may be threaded into the skull, which may have been drilled and tapped to receive the threaded portion of electrode holder 3404. Guide tube 3402 may include flat portions 3406 near the top of guide tube 3402 to assist in inserting guide tube 3402 with a wrench.

In FIG. 34B, once guide tube 3402 is in place in the skull, a tripod mechanism 3408 comes down over guide tube 3402 to allow adjustment of an angle of guide tube 3402 relative to the skull. Tripod mechanism 3408 is temporarily locked with a set screw to guide tube 3408 to prevent tripod mechanism 3408 from sliding up and down guide tube 3402. Feet 3410 of the tripod mechanism 3408 press against the skull but are not attached to the skull and their positions may adjustable using knobs 3412.

In FIG. 34C, the current tube angle relative to anatomy is monitored using a tracked array 3414 that is attached to the top of guide tube 3402. Array 3414 may freely rotate about an axis of guide tube 3402 since the system needs only to track the vector (line) down the center of guide tube 3402, which will be the path of the electrode.

A method or workflow using the system described herein may include the following steps. DRB 3200 may be attached to the skull of a patient and temporary skirt fixture 3300 may be attached to DRB 3200. A CT scan or O-Arm spin may be obtained to receive images of the target anatomy and system software may auto-detect BBs and auto-register tracking to the image.

After the scan, fixture 330 may be removed from DRB 3200.

Figure 35:
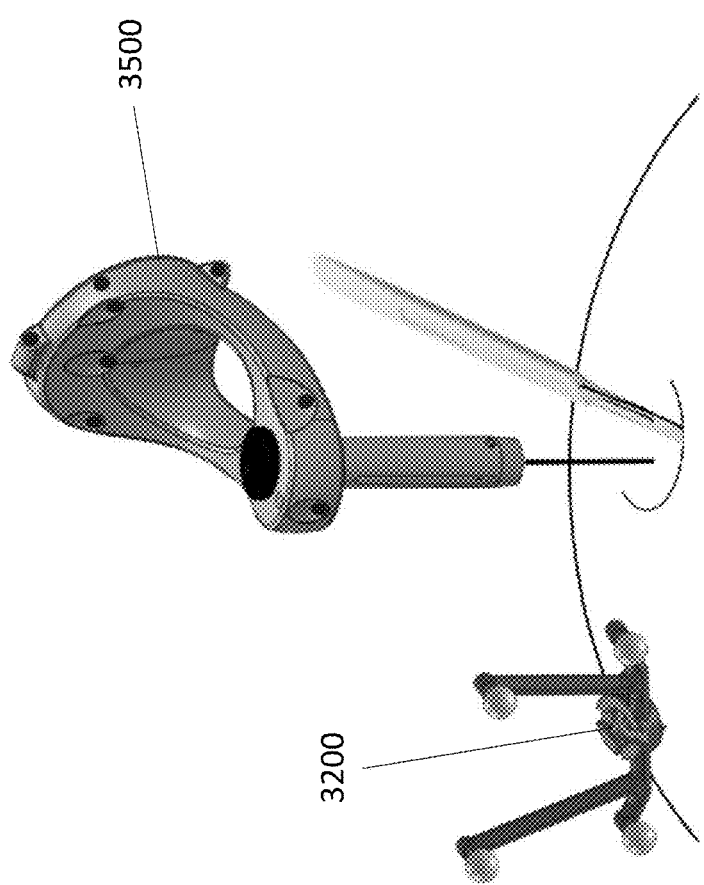
FIG. 35 illustrates a dynamic reference array and an end effector consistent with the principles of the present disclosure.

A trajectory may be planned of the electrode on the obtained medical images. These medical images may comprise the CT scan just obtained or merged Mill and CT scans. An end-effector 3500 of a robot may automatically move into place above the scalp of the patient. A laser held by end-effector 3500 may point to an entry location on the skin to assist in cutting a flap as shown in FIG. 35.

Figure 36:
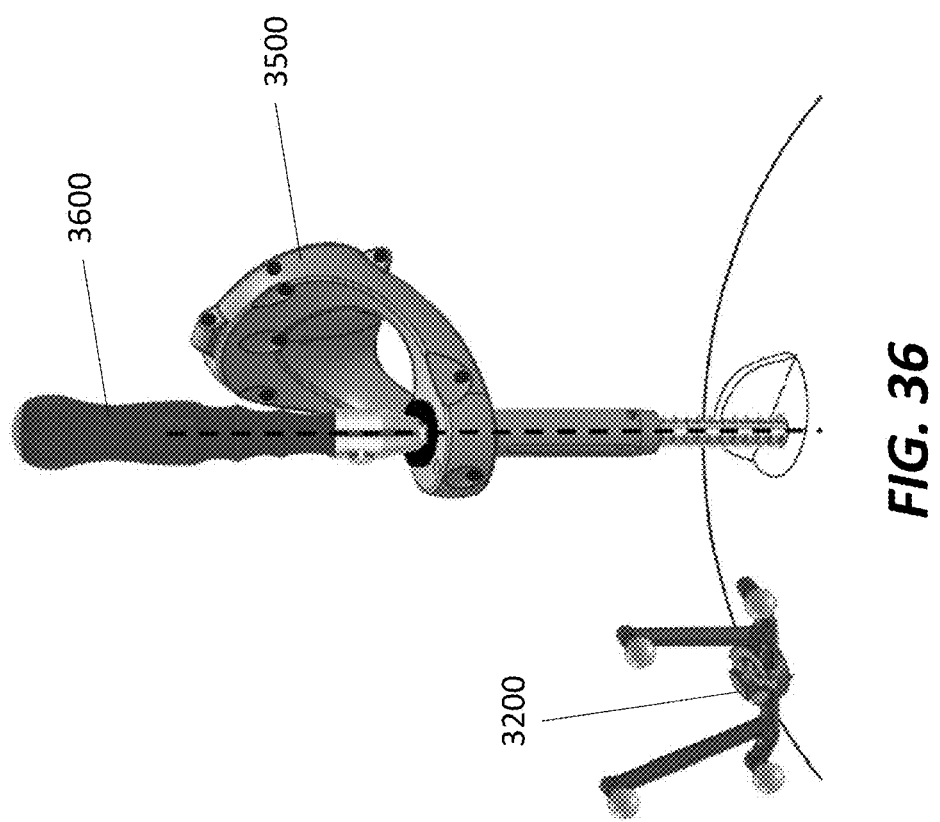
FIG. 36 illustrates a dynamic reference array and an end effector consistent with the principles of the present disclosure.

The skull may be exposed and a user may drill a craniotomy pilot hole while the robot guides the drill. The hole in the skull may be tapped to provide threads to lock to electrode holder 3404. As shown in FIG. 36, the robot may guide tap 3600.

Electrode holder 3404 may be screwed into the threaded hole, with the robot providing guidance for the location. The robot may then be removed, leaving electrode holder 3404 and guide tube 3402 as shown in FIG. 37.

Tripod mechanism 3408 is lowered into place over guide tube 3402. Feet 3410 may be adjusted so that tripod mechanism 3408 does not alter the orientation of guide tube 3402 while all three feet simultaneously touch the scalp. Additionally, the position of the tripod feet 3410 in their rotation about the guide tube 3402 may be adjusted so that they avoid contact with the DRB or other adjacent surgical equipment such as retractors. Once in place, tripod mechanism 3408 may be locked to guide tube 3402 with a set screw as shown in FIG. 38.

Figures 39A, 39B:
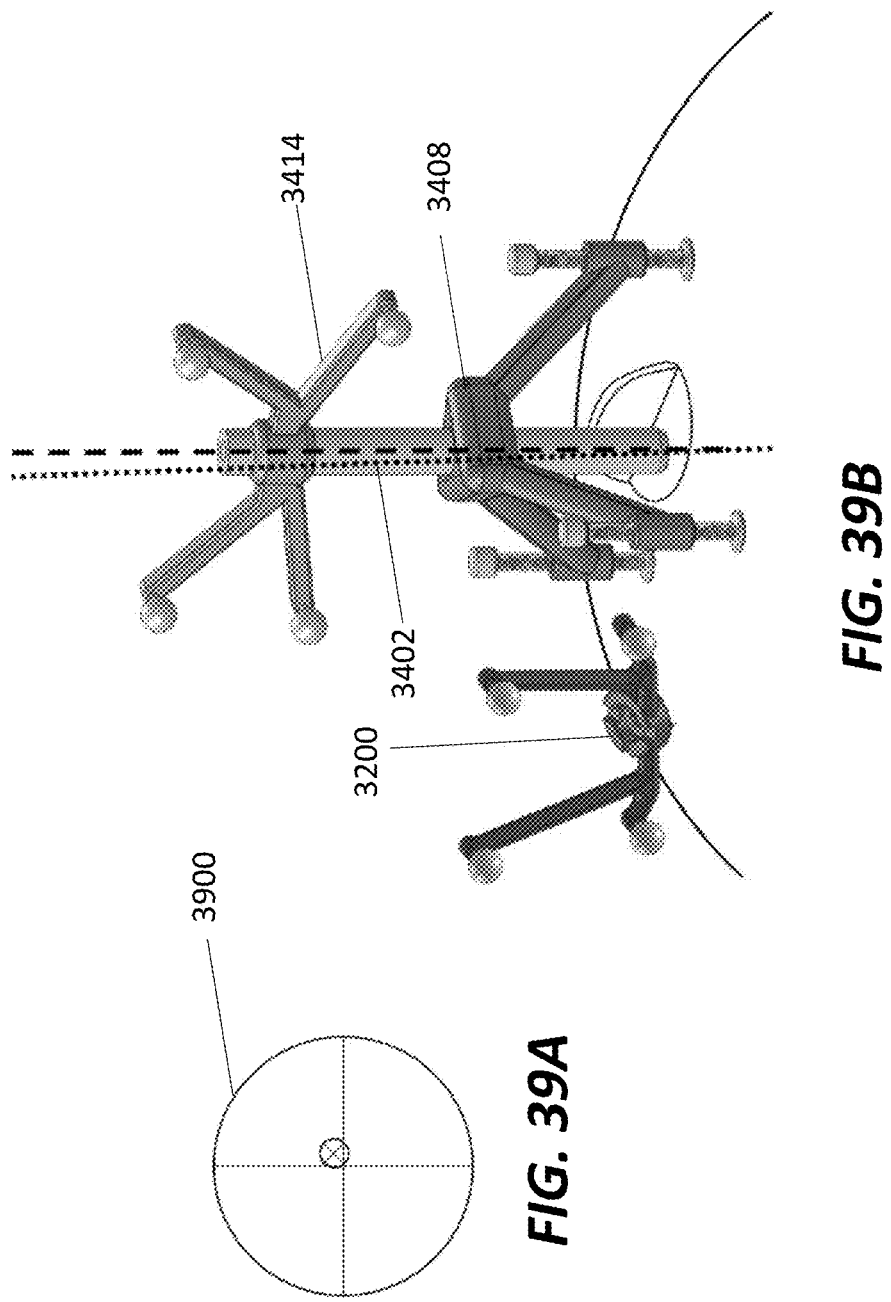
FIG. 39A illustrates a view of aligning a guide tube with a trajectory consistent with the principles of the present disclosure.
FIG. 39B illustrates a dynamic reference array, a guide tube with a detachable electrode holder and a tracking array, and tripod mechanism consistent with the principles of the present disclosure.

Tracking array 3414 may then be attached to the top of guide tube 3402 as shown in FIG. 39B. Alignment of guide tube 3402 is checked relative to the plan using navigation. Feet 3410 may be adjusted as necessary to match the plan.

A software feature may show a top-down view 3900 to assist in fine-tuning the trajectory as shown in FIG. 39A. Additionally, the system may provide software feedback on which of feet 3410 to adjust and in which direction by how many turns to adjust each. To do so, software may know the orientation of feet 3410 relative to DRB 3200, which can be determined by placing fiducials on each foot of the tripod, through natural fiducial recognition, or by the user specifying in a software interface how the feet are oriented.

An electrode is then inserted into guide tube 3402 through electrode holder 3404 to the desired depth within the brain. The guide tube 3402 is disengaged from electrode holder 3404 and removed, leaving behind electrode holder 3404. This method or workflow may be repeated for additional electrodes.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A tracking system for a cranial surgical operation comprising:
   a tracker base having a central hub and a plurality of tracking markers spaced from the central hub in a first predetermined pattern for viewing by tracking cameras, the central hub having a single through hole adapted to receive a single bone screw to be threaded into a skull, the single bone screw being the only bone screw required to fix the tracker base to the skull; and
   a fiducial base adapted to be attached to and detached from the tracker base in only one orientation, the fiducial base having a plurality of radiopaque markers arranged in a second predetermined pattern,
   wherein the central hub includes an anti-rotation structure adapted to mate with a corresponding structure in the fiducial base to prevent the fiducial base from rotating relative to the tracker base, and
   wherein the fiducial base includes:
      a ring having the plurality of radiopaque markers embedded therein: and
      a bar having the corresponding structure and attached to opposite ends of the ring through a central point of the ring.

2. The tracking system of claim 1, wherein the central hub includes a plurality of non-threaded spikes extending downwardly from a bottom surface of the central hub, to provide frictional stability without requiring additional screw holes into the skull.

3. The tracking system of claim 1, wherein the tracker base includes a plurality of arms extending laterally from the central hub with each arm having at least one tracking marker of the plurality of tracking markers.

4. The tracking system of claim 1, wherein the tracker base includes a plurality of legs extending upwardly from the central hub with each leg having at least one tracking marker of the plurality of tracking markers.

5. The tracking system of claim 1, wherein the tracker base includes:
   a plurality of arms extending laterally from the central hub with each arm having at least one tracking marker of the plurality of tracking markers; and
   a plurality of legs extending upwardly from the central hub with each leg having at least one tracking marker of the plurality of tracking markers.

6. The tracking system of claim 1, wherein the anti-rotation structure includes at least one notch.

7. The tracking system of claim 1, wherein the anti-rotation structure includes a plurality of notches asymmetrically arranged around the central hub.

8. The tracking system of claim 1, further comprising:
   a shaft for receiving an electrode;
   an adjustable stand having a plurality of height adjustable legs to allow adjustment of an angle of the shaft relative to the skull, the adjustable stand configured to slide over the shaft, wherein each leg is shaped to rest on the skull without being screwed to the skull.

9. A tracking system for a cranial surgical operation comprising:
   a tracker base having a central hub and a plurality of tracking markers spaced from the central hub in a first predetermined pattern for viewing by tracking cameras, the central hub having a single through hole adapted to receive a single bone screw to be threaded into a skull, the single bone screw being the only bone screw required to fix the tracker base to the skull;
   a fiducial base adapted to be attached to and detached from the tracker base in only one orientation, the fiducial base having a plurality of radiopaque markers arranged in a second predetermined pattern; and
   a navigation system having a plurality of cameras and adapted to register a medical image containing the plurality of radiopaque markers in an imaging space to an optical camera space for tracking based on the tracking markers visible to the plurality of cameras:
   wherein the central hub includes an anti-rotation structure adapted to mate with a corresponding structure in the fiducial base to prevent the fiducial base from rotating relative to the tracker base, and
   wherein the fiducial base includes:
      a ring having the plurality of radiopaque markers embedded therein; and
      a bar having the corresponding structure and attached to opposite ends of the ring through a central point of the ring.

10. The tracking system of claim 9, wherein the central hub includes a plurality of non-threaded spikes extending downwardly from a bottom surface of the central hub and providing frictional stability without requiring additional screw holes into the skull.

11. The tracking system of claim 9, wherein the tracker base includes a plurality of arms extending laterally from the central hub with each arm having at least one tracking marker of the plurality of tracking markers visible to the plurality of cameras.

12. The tracking system of claim 9, wherein the tracker base includes a plurality of legs extending upwardly from the central hub with each leg having at least one tracking marker of the plurality of tracking markers visible to the plurality of cameras.

13. The tracking system of claim 9, wherein the tracker base includes:
   a plurality of arms extending laterally from the central hub with each arm having at least one tracking marker of the plurality of tracking markers; and
   a plurality of legs extending upwardly from the central hub with each leg having at least one tracking marker of the plurality of tracking markers.

14. The tracking system of claim 9, wherein the anti-rotation structure includes a plurality of notches spaced apart from each other.

15. The tracking system of claim 9, wherein the anti-rotation structure includes a plurality of notches asymmetrically arranged around the central hub.

16. The tracking system of claim 9, further comprising:
   a shaft for receiving an electrode;
   a plurality of optical tracking markers attached to the shaft for tracking by the cameras of the navigation system;
   an adjustable stand having a plurality of height adjustable legs to allow adjustment of an angle of the shaft relative to the skull, the adjustable stand configured to slide over the shaft, wherein each leg is shaped to rest on the skull without being screwed to the skull.

\* \* \* \* \*